US012653777B2

(12) United States Patent
Klingman

(10) Patent No.: US 12,653,777 B2
(45) Date of Patent: *Jun. 16, 2026

(54) PRODUCTS AND METHODS FOR REDUCING MALODOR

(71) Applicant: LUMÊ DEODORANT, LLC, New York, NY (US)

(72) Inventor: Shannon Elizabeth Klingman, Chaska, MN (US)

(73) Assignee: Lume Deodorant, LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/902,969

(22) Filed: Jun. 16, 2020

(65) Prior Publication Data

US 2020/0330376 A1 Oct. 22, 2020

Related U.S. Application Data

(63) Continuation of application No. 14/613,420, filed on Feb. 4, 2015, now abandoned, which is a continuation (Continued)

(51) Int. Cl.
| | |
|---|---|
| *A61K 9/00* | (2006.01) |
| *A61K 8/02* | (2006.01) |
| *A61K 8/365* | (2006.01) |
| *A61K 9/70* | (2006.01) |
| *A61K 31/19* | (2006.01) |
| *A61K 31/192* | (2006.01) |
| *A61K 31/20* | (2006.01) |
| *A61P 31/04* | (2006.01) |
| *A61Q 15/00* | (2006.01) |

(52) U.S. Cl.
CPC .......... *A61K 9/0034* (2013.01); *A61K 8/0208* (2013.01); *A61K 8/365* (2013.01); *A61K 9/7007* (2013.01); *A61K 31/19* (2013.01); *A61K 31/192* (2013.01); *A61K 31/20* (2013.01); *A61Q 15/00* (2013.01)

(58) Field of Classification Search
CPC .... A61K 9/0034; A61K 8/0208; A61K 8/365; A61K 9/7007; A61K 31/19; A61K 31/192; A61K 31/20; A61Q 15/00; A61P 31/04

See application file for complete search history.

(56) References Cited

U.S. PATENT DOCUMENTS

| | | | |
|---|---|---|---|
| 5,091,171 A * | 2/1992 | Yu ......................... | A61K 8/4953 424/642 |
| 6,231,259 B1 * | 5/2001 | Murgida ................ | A61K 8/585 401/175 |

(Continued)

FOREIGN PATENT DOCUMENTS

| | | | | |
|---|---|---|---|---|
| EP | 0775486 A1 * | 5/1997 | ........... | A61Q 17/005 |
| EP | 2086497 B1 * | 7/2013 | ........... | A61K 8/0229 |

OTHER PUBLICATIONS

Google English Translation of EP0775486A1 (Year: 1997).*
EP2086497B1—Google English Translation (Year: 2009).*

*Primary Examiner* — Kyung S Chang
(74) *Attorney, Agent, or Firm* — FLOREK & ENDRES PLLC

(57) ABSTRACT

Products and methods are disclosed for reducing the production of unwanted odors from the pudendum.

3 Claims, 7 Drawing Sheets

Related U.S. Application Data of application No. 12/875,123, filed on Sep. 2, 2010, now abandoned.

(60) Provisional application No. 61/309,831, filed on Mar. 2, 2010, provisional application No. 61/289,992, filed on Dec. 23, 2009.

(56) References Cited

U.S. PATENT DOCUMENTS

| 2005/0031565 A1 * | 2/2005 | Prud'Homme | A61K 8/06 |
| | | | 424/65 |
| 2007/0116656 A1 * | 5/2007 | Schulz | A61Q 15/00 |
| | | | 424/68 |
| 2007/0172440 A1 * | 7/2007 | Schulz | A61K 8/26 |
| | | | 424/68 |

* cited by examiner

PRODUCTS AND METHODS FOR REDUCING MALODOR

CLAIM TO PRIORITY

This application claims priority to U.S. patent application Ser. No. 14/613,420, filed Feb. 4, 2015 by Shannon Klingman, which claims priority to U.S. patent application Ser. No. 12/875,123, "Products and Methods for Reducing Malodor from the Pudendum," filed Sep. 2, 2010 by Shannon Klingman, which claims priority to U.S. Patent Appl. Ser. No. 61/309,831, "Products and Methods for Reducing Malodor from the Pudendum," filed Mar. 2, 2010 by Shannon Klingman, and also U.S. Patent Appl. Ser. No. 61/289,992, "Products and Methods for Reducing Malodor from the Pudendum," filed Dec. 23, 2009 by Shannon Klingman, all of which are hereby incorporated by reference in their entireties for all purposes.

BACKGROUND

Field of the Invention

This invention pertains to products and methods for personal care, particularly for reducing or preventing unwanted odor from the pudendum.

Description of Related Art

Fishy odors from the pudendal region or genitalia of the female body have long been a source of annoyance and embarrassment to adult and teenaged women. Women seeking help from physicians are frequently given antibiotics such as metronidazole, based on the long-standing belief that vaginal bacteria are the cause of the problem. Indeed, a fishy odor is commonly considered to be a symptom for bacterial vaginosis (see, for example, "Bacterial Vaginosis," *Wikipedia*, http://en.wikipedia.org/wiki/Bacterial_vagino-sis, accessed Nov. 17, 2009). Others seeking relief have tried a variety of products such as douches which may provide only short-term decrease in the odor (if the vagina was the actual source of the odor). In spite of many medications and feminine hygiene products, there has been a long-standing unmet need in this area, fueled by lack of understanding about the causes and the nature of the problem, especially the assumption that fishy odor only arises from the vagina due to bacterial imbalance or infectious cause such as bacterial vaginosis and trichomonas.

The "Whiff test" for vaginosis involves treating body fluids with potassium hydroxide (KOH). A resulting fishy odor produced by an amine reaction is taken as an indicator for the presence of anaerobic bacteria. However, the amine reaction or related reactions that result in a fishy odor can take place without addition of KOH, but under other elevated pH conditions on the pudendum. The materials serving as a source for the nitrogen-containing compounds released as fishy odor (e.g., trimethylamine) can include semen, blood, urine, cervical mucus and post menopausal physiologic discharge. When these are brought in contact with the anaerobic bacteria from the rectum, an unpleasant fishy odor will result. The odor is known to be associated with reactions from bacteria, but the historic focus on bacteria in the vagina and the assumption that vaginitis or more specifically, bacterial vaginosis, is the cause of the odor may have misled many in seeking for solutions that treat bacteria in the vagina.

We have found that for many women, the source of the odor is more commonly from the pudendum (including the intergluteal folds and external genitalia), where anaerobic bacteria from the lower gastrointestinal (GI) tract or other sources can be found. These anaerobic bacteria may be especially present on the external skin around the perianal anatomy.

The new recognition that vaginal bacteria are not cause of fishy odor in many women is of special significance, and helps explain why antibiotic treatments and other standard treatments have fared so poorly in treating many cases of fishy odor, and why may women presenting symptoms of fishy odor do not actually have bacterial vaginosis when thorough testing is conducted (see, for example, N. K. Lowe et al., "Accuracy of the Clinical Diagnosis of Vaginitis Compared With a DNA Probe Laboratory Standard," *Obstetrics & Gynecology*, vol. 113, no. 1, January 2009, pp 89-95, abstract available online at http://journals.lww.com/greenjournal/Abstract/2009/01000/Accuracy_of_the_Clinical_Diagnosis_of_Vaginitis.15.aspx and Hope K. Haefner, "Conquering Resistant Vulvovagini-tis," 2007, presentation available online at http://www.yel-lowdocuments.com/12180308-advancements-in-benign-vulvar-and). It also points to the long unmet need for improved means of reducing or preventing fishy odor by better controlling the activity of anaerobic bacteria on the pudendum, particularly those interacting with or feeding on nitrogen compounds in body fluids such as semen, blood, urine, and feces.

It is believed that a particularly significant discovery is the recognition that the source of a fishy odor for many women is not bacteria in the vagina, nor bacteria coming from the vagina, but anaerobic bacteria from non-vaginal sources such as the gastrointestinal tract. An understanding of this discovery can be enhanced in part by consideration of a rare metabolic disorder, trimethylaminuria, a disorder occurring when humans have an impaired version of the enzyme flavin-containing monooxygenase 3 (FMO3), which converts trimethylamine to trimethylamine N-oxide during the metabolism of some nitrogen-containing compounds such as choline or phosphocholine. With impaired FMO3 activity, trimethylamine concentrations become elevated and strong fishy odor can be generated by the sweat and other body fluids of a person, making life difficult and painful. Foods rich in choline are especially problematic for those with trimethylaminuria, since it leads to production of large amounts of trimethylamine. Without wishing to be bound by theory, it is believed that the release of trimethyl amine and possibly other nitrogenous compounds produced by anaero-bic bacteria at elevated pH on the pudendum of the human body is analogous to the production of trimethylamine in the body when oxidizing enzymes are impaired in those suffer-ing from trimethylaminuria. Again, without wishing to be bound by theory, recognition of this analogous condition in light of the newly recognized mechanisms for fishy odor generation on the skin of the pudendum also suggests that semen may be an especially important component in the production of fishy odor in some cases, for semen, of all body fluids, may be the richest in choline and is among the richest natural sources of choline and water-soluble choline compounds, and thus is believed to be a highly significant potential source for trimethylamine production by certain anaerobic bacteria on the pudendum.

Thus, we have discovered that the introduction of semen, blood, urine, feces, and other body fluids into the pudendum, including the perineum and adjacent regions, can raise the pH on the skin and provide the nitrogenous materials and alkaline conditions for bacterial-assisted production of significant amounts of volatile amine compounds such as trimethylamine, giving rise to a fishy odor. While the reactions involved may be similar to those that occur from bacterial vaginosis, fishy odor can be produced on the pudendum under benign conditions. In other words, the vagina is not the key factor when trying to solve the problem of transient fishy odor for most women.

For effective prevention of the fishy odor from the amine reaction, wiping or washing alone is inadequate. The pH of the environment of the perianal bacteria needs to be maintained in an acidic state such as at a pH less than about 5.5, or less than about 5.3, or less than about 5.1, in order to hinder the amine reaction that causes the unwanted fishy odor. 3.5 to 4.2 is the normal range of the pH of the vagina, and a pH in this range can be suitable for the pH of the pudendum. Thus, a suitable range for pH may be, by way of example, from about 3 to about 5.5, from about 3.2 to about 5, from about 3.5 to 4.5, or from about 3.5 to 5.0. Without wishing to be bound by theory, our work indicates that the release of the fishy odor can be triggered by an amine reaction that occurs when the anaerobic bacteria of the pudendum come into contact with alkaline bodily fluids such as semen, blood, feces, and other agents such as soap, in essence, giving a positive Whiff test on the external genitalia. Possible insight into related mechanisms may be found, again without wishing to be bound by theory, in the study of Y. Tsuchiya and E. Endo, "Enzymatic Reductto-hoion of Trimethylamine Oxide," *Tohoku Journal of Agricultural Research,* 1952, pp. 127-133, available online at http://ir.library.tohoku.ac.jp/re/bitstream/10097/29074/1/KJ00000713720.pdf, which describes how a bacterial enzyme, triamineoxidase, activates relatively odorless trimethylamine oxide and renders it susceptible to reduction to the highly malodorous trimethyl amine by various dehydrogenases. Several potential inhibitors of the reaction are explored. On page 130 of Tsuchiya and Endo, results for the reaction rate for trimethylamine production as a function of pH shows that a pH above 5.5 such as from about 6 to 8 favors high levels of trimethylamine, whereas a pH of 5.5 or less, or 5.0 or less, favors low levels of trimethylamine.

An understanding of the importance of maintaining a low pH in the external environment of the pudendum relative to the issue of controlling fishy odor appears to be lacking in prior attempts to deal with fishy odor. For example, some commonly used products employ baking soda, an alkaline compound, and a recognition of the role of the environment external to the vagina and its pH appears to have been lacking in terms of controlling fishy odor.

The compositions and methods proposed herein for controlling fishy odor arise in part from the surprising realization that the real problem in most cases is not bacteria in the vagina, but conditions arising from an anatomically inevitable consequence of intercourse, due to semen form intercourse, leaking urine, and blood from monthly cycles coming in contact with the perianal bacteria that can inhabit various parts of the pudendum. The close physical proximity of the vulvar and perianal regions contributes to the presence of bacteria that can produce or participate in reactions leading to generation of trimethylamine or related fishy odor compounds, feeding upon the nitrogenous compounds coming from intercourse, urine, menstruation, feces, etc.

With a realization of the nature of the origin of fishy odors due to elevated pH and associated conditions in the pudendum, we were able to subsequently develop what is believed to be the first product that addresses the real problem (for many women) over a prolonged period of time.

Vinegar wipes, douches, and other acidic products have been proposed for personal cleansing, but such products have generally been developed for rapid cleansing and not for lasting control of pH. Thus, even highly acidic vinegar wipes only provide a short-term change in pH, as the acidic components is applied and then wiped or washed off or otherwise neutralized or quickly removed from the skin. With the viscous carrier of many embodiments disclosed herein, acidifying components can be available for a prolonged period of time to effectively control the pH of the environment. Further, with larger molecular weight alpha-hydroxy acids disclosed herein (for many embodiments) that do not rapidly penetrate the skin, the alpha-hydroxy acids can remain on or above the skin to effectively maintain the pH in a suitable range for a prolonged period of time, unlike much lighter acids.

Thus, there is a need for new products and methods that can address the surprising discoveries regarding the sources of fishy odor in many women, and that can overcome the long-standing unmet needs that have not been adequately addressed by previous products, formulations, and methods.

Many retail and prescription products have been marketed are directed at treating bacteria in the vagina, which again do not address the issue of the external environment in the pudendum. Most on the retail side are a cover-up with baking soda and perfumes or other ingredients that do not address the problem or may even exacerbate it at the true source (albeit the previously unrecognized source).

The recognition that the source of the fishy odor is frequently from the pudendum and not from the vagina helps explain, in retrospect, why treatments based on attacking bacteria on the vagina have been relatively ineffective for so many women for so long, and may also help explain why misdiagnosis of vaginosis is such a common problem (see "Throwing the Dice for the Diagnosis of Vaginal Complaints?" by Andreas Schwiertz et al., *Annals of Clinical Microbiology and Antimicrobials,* Vol. 5. No. 4, 2006, available online at http://www.annclinmicrob.com/content/5/1/4). The new understanding of the need to provide long-term control of pH on the skin of the pudendum also helps explain, in retrospect, why previous solutions employing wipes and other means did not provide lasting or effective solutions. What is needed, then, is an effective system or method for providing a suitable acidic pH over a prolonged period of time in the pudendum or portions thereof such that the amine reactions giving rise to a fishy odor can be impeded, resulting in a significant decrease in the production of unpleasant odors.

In spite of the surprising discovery that a major source for fishy odor was not from the vagina itself but from the external skin of the pudendum, particularly when the pH was elevated by the presence of semen, blood, or other materials or factors, we found that various efforts to decrease pH were not necessarily adequate to provide an acceptable solution, for, among other reasons, there is a risk of skin irritation or other unwanted responses with prolonged exposure to many acidic compounds. For effective treatment of the newly appreciated causes of unwanted fish odor for many women, we have also discovered that a lasting reduction in fishy odor and associated problems of the inevitable chronic presence of anaerobic bacteria in the pudendum require new strategies to provide sustained pH control in ways that do not irritate the skin. Thus, there is a long-standing need to provide sustained pH control in non-irritating means to reduce the common problem of fishy odor production from the pudendum.

SUMMARY

We have found that relatively non-irritating alpha-hydroxy acids such as mandelic acid or combinations of mandelic acid and other alpha-hydroxy acids such as lactic acid, in combination with a suitable carrier such as a protective lipophilic carrier, a bioadhesive, or a suitable wipe formulation, can provide acidifying agents that are effective in controlling the pH in the pudendum while not irritating the skin. By virtue of the acidic environment provided by such compositions, the reactions that produce fishy odor on the pudendum can be controlled such that the odor is substantially reduced or eliminated. In many embodiments, the acidifying agents can remain active in the pudendum over a prolonged period for lasting odor reduction. Such compositions may be applied to the body in a variety of ways, such as by application using a pretreated wipe, pad, or absorbent article containing the acidifying composition that transfers to the body, or by direct application to the body using a spray or other dispenser or by application using the fingers or other means to apply the composition onto the pudendum.

As used herein, "pudendum" refers to the external genitalia and surrounding regions of the body, including the interlabial folds, the clitoral region, the perineum, the perianal region, the vulvar and perivulvar regions, and the intergluteal folds.

As used in the description, and in the claims, the term "alpha-hydroxy acid" refers to compounds represented by the following generic structure:

(R1)(R2))C(OH)COOH where R1 and R2 are H, alkyl, aralkyl or aryl groups. In addition, R1 and R2 may carry OH, CHO, COOH and alkoxy groups. Typical alkyl, aralkyl and aryl groups for R1 and R2 include methyl, ethyl, propyl, isopropyl, butyl, pentyl, octyl, lauryl, stearyl, benzyl and phenyl etc. The alpha-hydroxy acids include, but are not limited to, lactic acid, mandelic acid, glycolic acid, malic acid, 2-hydroxyoctanoic acid, 2-hydroxydecanoic acid, and citric acid. In some embodiments, the alpha-hydroxy acid has 13 or fewer carbons, 12 or fewer carbons, 11 or fewer carbons, 10 or fewer carbons, 9 or fewer carbons, or 8 or fewer carbons, such as between 2 and 14 carbons, between 2 and 11 carbons, between 3 and 11 carbons, between 3 and 13 carbons, between 7 and 12 carbons, or between 8 and 12 carbons. In one embodiment, the alpha-hydroxy acids comprise a mixture of 3-carbon and 8-carbon alpha-hydroxy acids.

To provide an effective quantity of a suitable alpha-hydroxy acid in the environment on the pudendum, a viscous carrier substantially more viscous than water can be effective in retaining the material. As used herein, a material such as a liquid is said to be "viscous" when it has a viscosity of from about 6 mPa·s (millipascal-seconds) to about 300,000 mPa·s when measured at 25° C., more specifically from 15 mPa·s to 150,000 mPa·s, and more specifically still from 50 mPa·s to 150,000 mPa·s. Viscosity herein is measured on neat composition using a Brookfield RVT, T-C Spindle at 5 rpms and Heliopath Stand, as described in US Pat. Application 20060002876, "Personal Care Compositions with Improved Hyposensitivity," published Jan. 5, 2006 by C. M. Cahen, herein incorporated by reference to the extent that it is noncontradictory herewith. In general, a viscous compositions has a viscosity that is substantially greater than that of water, and typically provides improved application characteristics when compared with products having a viscosity similar to that of water when applied directly by the user using manual (i.e. hand) application.

A lipophilic viscous carrier such as a cream can further protect the skin and reduce risks of irritation from the alpha-hydroxy acid. One or more suitable alpha-hydroxy acids in combination with a viscous lipophilic carrier can be applied to the pudendum using the fingers or via a wipe or pad, or can be transferred from another article such as the pretreated surface of an absorbent feminine pad such as a pantiliner. In typical embodiments, the composition is only applied to the pudendum or other external skin and is not applied to the vagina. Indeed, indicia or other information associated with compositions within the scope of the present invention may direct the user to not apply the composition within the vagina, and may further indicate that the formulation is intended for application only to the pudendum if prevention or reduction of fishy odor is desired, or for improved health of the pudendal region.

Thus, in one aspect, a product is disclosed for application to the pudendum of a user to reduce fishy odor, the product comprising about 0.5 weight percent or greater mandelic acid in a viscous lipophilic carrier, the product being physically associated with indicia specifying that the product should be applied to the pudendum. As used herein, "physically associated with" refers to indicia on an item physically proximate to the product to enable a user to obtain the information or directions given by the indicia, and more specifically refers to indicia such as printed instructions located on a container that contains the products or on a label or other printed surface connected to a container of the product or its associated packaging. Examples can include instructions disposed on or near a dispenser of the product, a printed card intended to be distributed with the product and provided near or attached to the packaging, or a label on a tube or tub that contains the product. Indicia need not be physically printed with ink but may be displayed in other ways, including electronic display on electronic paper or other display means physically associated with the product.

Compositions within the scope of the present invention may be provided in the form of pre-treated wipes, including wet wipes or wipes pretreated with a viscous lotion, or may be applied to a wipe shortly before contacting the wipe to the pudendum or any part thereof. In one embodiment, for example, a cream comprising one or more suitable alpha-hydroxy acids is applied to a wipe, including a dry wipe or a wet wipe, prior to use. The wipe may be packaged with the cream already in contact therewith, or may be packaged with or marketed in association with a quantity of the cream that can be manually applied to the wipe prior to contacting the wipe with the pudendum, such that the cream is transferred to the pudendum. As used herein, a "cream" is generally an emulsion having a kinematic viscosity of greater than 500 centistokes, typically in the range of 10,000-50,000 centistokes.

The carrier need not be lipophilic and may, for example, comprise an aqueous gel or other aqueous bioadhesive comprise a hydrated polymer. Alternatively, a substantially aqueous, low-viscosity carrier may be used similar to traditional water-based wet wipe formulations, but comprising a suitable alpha-hydroxy acid. For the alpha-hydroxy acid to remain effective on the pudendum for a prolonged period of time after application with a wet wipe-style product, additional measures may be taken such as encapsulation of at least a portion of a quantity of an alpha-hydroxy acid for sustained release thereof, or providing of delivery means for sustained contact of a low-pH solution with a portion of the pudendum.

In some versions, the with one or more suitable alpha-hydroxy acids is provided in a container or with a kit that contains or is physically associated with indicia instructing the user that the composition is to be applied to the pudendum. The indicia may indicate that the composition should only be applied to pudendum or more generally that it is intended for use on the pudendum or should be applied on the pudendum. The indicia may further specify suggested methods for repeat application, including time intervals or conditions which would require more frequent application. In some versions, the indicia indicate that the product can help control fishy odor arising from the pudendum, and may indicate the benefit can be obtained by maintaining a suitable pH range in the environment on the pudendum.

In one aspect, a composition is disclosed which comprises a viscous lipophilic carrier and at least 1% by weight of an alpha-hydroxy acid having a molecular weight of at least 125 or at least 140 (the molecular weight of mandelic acid is about 152), or having at least 1% by weight of mandelic acid or a derivative thereof. In some versions, the alpha-hydroxy acid may have a solubility in water of at least 1 gram per 10 ml of water (mandelic acid has a solubility of 1 gram in 6.3 ml of water) at 25° C., and/or may have an acidity expressed as pKa of at least about 2.0 or at least about 3.0 (larger numbers indicate weaker acids; mandelic acid has a reported pKa of 3.37 and lactic acid has a reported pKa of 3.86). The composition may be provided in a container provided with indicia instructing users to apply the composition to the external skin of the pudendum, and may further specify that so doing will help reduce undesirable odor or the bacteria that cause such odor, and may further indicate that odor control can thereby be provided over a prolonged period of time.

In another aspect, a method is disclosed for reducing undesirable odors arising from the pudendum of a user, the method comprising: a) providing a composition comprising at least 0.5% by weight of mandelic acid or a derivative thereof disposed in a viscous substantially lipophilic carrier, and b) instructing a user to apply the composition to the user's pudendum.

The method may further comprise making a claim that the composition is effective in reducing fishy odor, and may also include further instructing the user to repeat application of the composition to the pudendum after a prolonged period of time has occurred and/or after exposure to conditions likely to elevate the pH of the environment of the pudendum, such as intercourse, contract with blood or feces, or bathing with soap.

In one aspect, a wipe product is disclosed for reducing the production of unwanted odor from the pudendum, the product comprising an openable enclosure containing at least one wipe pretreated with an acidifying composition, the acidifying composition comprising at least about 0.5% by weight of a first alpha-hydroxy acid comprising at least 7 carbons, having a molecular weight in the range of about 135 to about 400, and having no more than one carboxylic acid group for every 7 carbons, the acidifying composition having a pH of from about 3.5 to about 4.5 and further comprising at least 50% by weight of a viscous lipophilic carrier, wherein upon wiping the pudendum with one of the at least one wipes, the acidifying composition is adapted to transfer in part to the pudendum and have a substantial portion thereof remain in contact with the pudendum for a prolonged period of time after wiping, thereby effectively lowering the pH on the treated portion of the pudendum for a prolonged period of time. The acidifying composition may comprise mandelic acid or its derivatives, and in related embodiments mandelic acid in an effective amount is present in combination with one more additional alpha-hydroxy acids such as lactic acid, in a substantially lipophilic carrier having rheological properties of a bioadhesive or otherwise have sufficient non-Newtonian properties (e.g, a relatively high yield stress) such that it does not readily flow off the body under the influence of gravity after application to the body. Other alpha-hydroxy acids that may be considered in various embodiments.

As used herein, a material with a relatively high yield stress may be said to "not substantially flow in response to gravitational force" or "not readily flow off a surface under the influence of gravity" if, when applied uniformly to a vertical surface such as a vertical sheet of clean sodium glass with the applied layer having a thickness of 2 millimeters over a 2 cm×2 cm area defining a square with top and bottom sides parallel to the horizontal plane, the effect of gravity in redistributing the applied material is relatively minor such that after 30 seconds of exposure to gravity, the upper half of the square (a 2 cm×1 cm region of the coated area) still has at least 30% of the originally applied mass (with no flow at all, it would have 50% of the originally applied mass). The test should be done at 23° C.

In some embodiments, a first alpha-hydroxy acid such as mandelic acid and optionally a second alpha-hydroxy acid composition, such as lactic acid or other acids, is combined to provide a long-lasting acidifying composition that can control the pH of the pudendum after application for a prolonged period of time such as at least about 10 minutes, 30 minutes, 60 minutes, 6 hours, 12 hours, or 24 hours. Indeed, in some embodiments, it has been found that a single treatment with compositions described herein can provide effective control in preventing fishy odor for periods of 24 hours or longer.

In some embodiments, the carrier can be a lipophilic carrier such as a cream comprising an oil/water emulsion and having a finite yield stress to allow substantial quantities to remain in contact with the body after application over a prolonged period of time. Yield stress may be measured using a static vane-based test method with the Brookfield YR-1 of Brookfield Engineering Laboratories (Boston, MA). The yield stress at 25° C. may be, for example about 2 kPa s or less, or about 1 kP s or less, or about 0.2 kPa s or less. Other techniques for providing sustained presence of acids may be considered in various embodiments, including the use of time-release encapsulation technology or barriers that release the actives when triggered by moisture, pH, activity, or other conditions.

The carrier can be made from a variety of known agents. It may comprise a viscous, lipophilic base that is substantially water free or is a mixture of lipophilic components and an aqueous solution such as an emulsion. The carrier may also be a hydrophilic base such as a gel, including bioadhesive gels, or a solution such as the wetting solution of a wet wipe. The carrier may also be a foam or other forms discussed herein.

In one version, a composition for preventing fishy odor is delivered using a wipe. The wipe may be provided with the composition already present, such as a wet wipe or impregnated wipe holding the viscous carrier and active ingredients. Alternatively, the composition may be provided separately for the user to apply using a wipe or other substrate such as a tissue. In one version, a single-use pouch or kit comprises a wipe and a separate dose of the composition that can be released on to the wipe prior to application.

The composition according to selected embodiments of the present invention may have a pH (as measured, for example, with pH test trips at 22° C.) of about 3.0 to about 5.0, or from about 3.2 to about 4.5, or from about 3.3 to 4.2, such as from about 3.5 to about 4.2.

Compositions according to selected embodiments of the present invention can be provided in a wide variety of forms, such as gels, creams, foams, impregnated pads or strips, and the like, many of which can be suitable for prolonged contact against the human body. Prolonged contact can be achieved direct application of the active ingredients onto the skin by any known means, including the use of bioadherents, or by mechanical means in which an article comprising a composition of the present invention is held in place against the body by, for example, contact with underwear or other clothing.

Some forms of useful products are intended for brief contact with the human body, such as wet wipes or treated pads that may make brief contact with the skin of the pudendum to deliver active ingredients, though in such products, the active ingredients may be provided in a composition that remains on the skin to provide protection over a prolonged period of time. Compositions of selected embodiments of the present invention may also be provided in forms intended for direct application to the human body such as rinses, washes, sprays, and the like.

For embodiments in which a formulation is applied using a wipe, the wipe can serve not only to deliver the active ingredients to lower the pH on the body over a prolonged time but also to mechanically remove debris. Methods of use could include daily treatment such as after bathing to clean and acidify the pudendum. The treatment could include use of a prepackage, pretreated wipe or of an ordinary wipe that is wetted or coated with a formulation as described herein.

In other embodiments, at least one active ingredient may be in substantially dry or solid form, such as a powder attached to or disposed within a pad. When wetted by water or aqueous fluids prior to, during, or after application of the active ingredient to the body, the active ingredient may at least partially dissolve to more effectively control the acidity of the environment (e.g., that of material on the skin of the pudendum) or to deliver other benefits.

In another aspect, a method is disclosed for reducing or preventing malodor from the pudendum, comprising: (a) providing a user with a product comprising an acidifying composition having at least about 0.5% by weight of mandelic acid, said acidifying composition having a pH between about 3.2 and 4.5, and (b) providing directions to the user to apply the acidifying composition to the pudendum. The acidifying composition may further comprise at least about 1% by weight of a second carboxylic acid component such as lactic acid. In some embodiments of the method, the acidifying composition may have a non-zero yield stress and the directions for use are adapted to cause the acidifying composition to effectively remain in contact with the human body for a period of at least 10 minutes after applying the acidifying composition to the pudendum according to the directions. The acidifying composition may have a lipophilic carrier or be in the form of an aqueous solution or may comprise an aqueous solution, and may be substantially hydrophilic. The product and the directions may be adapted such that the composition, when applied according to the directions, will be effectively kept in contact with the pudendum for a period of at least 60 minutes, and wherein the pH on the skin in contact with the composition is between about 3.5 and 4.5 during a majority of the at least 60 minutes. Skin pH can be measured with dry pH electrodes, as is known in the art. See, for example, B. Eberlein- Konig et al., *Acta Derm Venereol.* 2000, vol. 80, pp. 188-191, available online at http://adv.medicaljournals.se/files/pdf/80/3/188-191.pdf.

The method may further comprise (c) providing one or more wipes for use with the product, and the step of providing directions to the user may then include providing directions to transfer the product from at least one of the one or more wipes to the pudendum.

DETAILED DESCRIPTION OF THE DRAWINGS

Figure 1A:
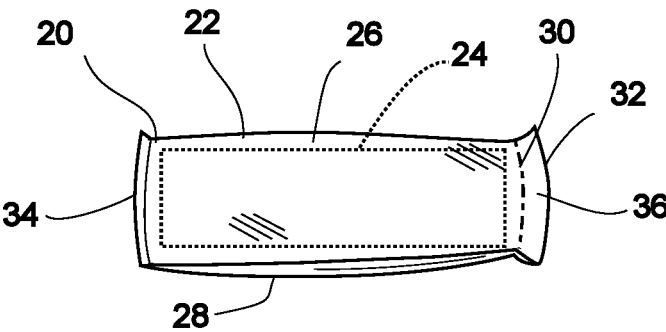
FIGS. 1A, 1B, and 1C show views of a wipe originally sealed in a pouch, the wipe comprising a formulation for reducing malodor.

FIG. 1A depicts an individual use product 20 containing a folded wet wipe 24 sealed within a sealed pouch 22, the wipe 24 comprising a formulation (not shown) for reducing malodor in the pudendum. The pouch 22 may be made of a film or foil wrap or any other suitable flexible materials, and generally comprises a front side 26, a back side 28, a top end 32, and a bottom end 34, the top end 32 comprising a tear line 30 which may be perforated, for example, and a tear-away portion 36 which is removed by tearing along the tear line 30 to open the pouch 22. Of course, many alternative means may be used to provide for opening the pouch 22, including resealable flaps (not shown), tear lines along any region of the pouch 22, slidable or resealable closures (not shown) such as those commonly used in sandwich bags, and the like. In related embodiments not shown here, multiple wipes may be disposed in a pouch 22.

Figure 1B:
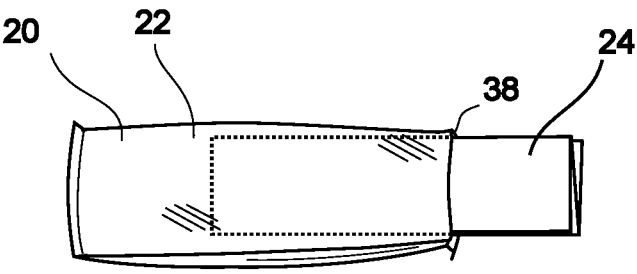

FIG. 1B depicts the pouch 22 of FIG. 1A after the tear-away portion 36 thereof has been removed, opening the pouch 36. As depicted, the wipe 24 has been partially removed from the pouch 22. The wipe 24 is a folded wipe with a Z-style fold, though any suitable folded configuration may be used.

Figure 1C:
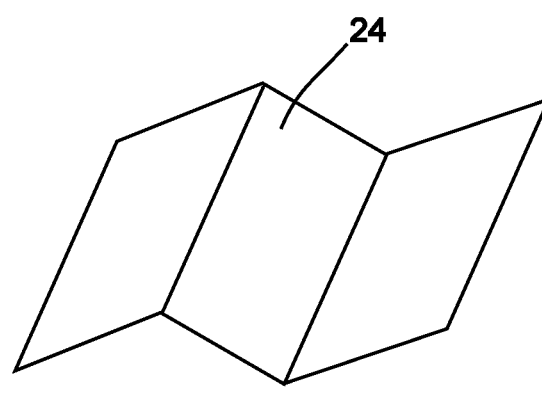
Figure 2:
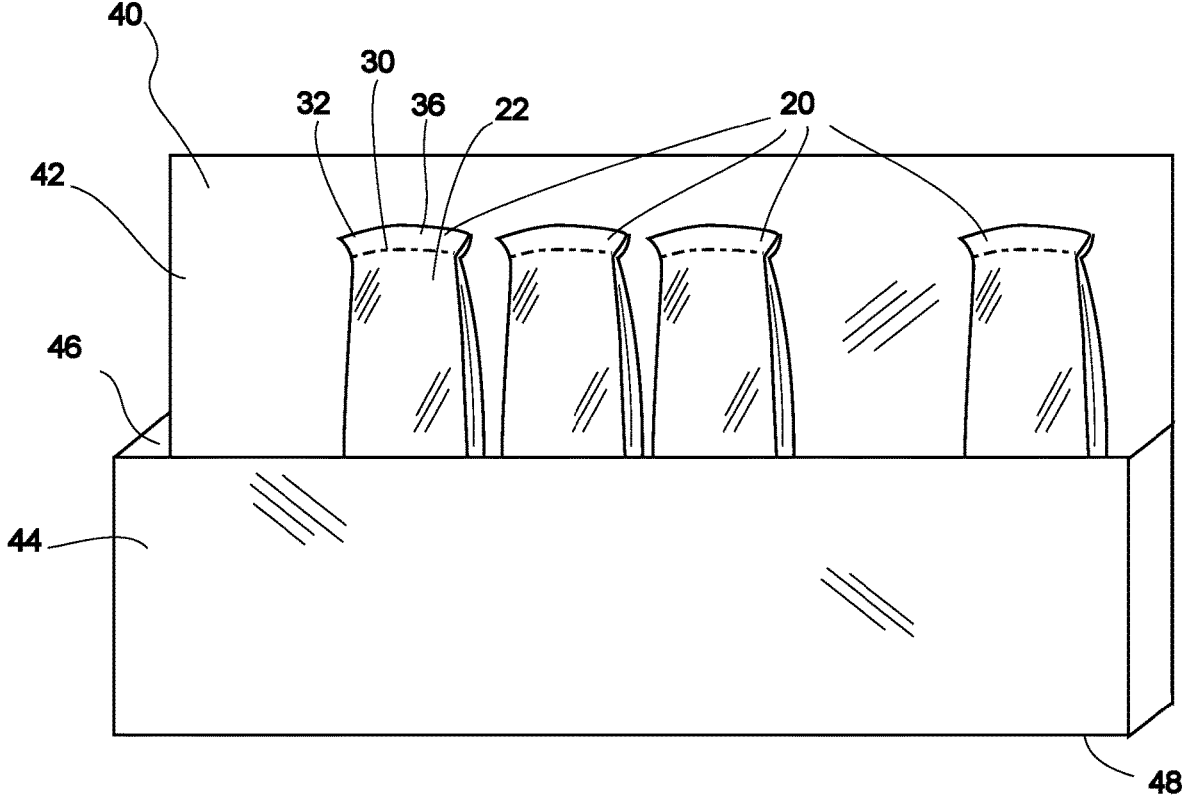
FIG. 2 shows one version of a container holding multiple individually sealed wipes for reducing malodor.

FIG. 1C shows the wipe 24 of FIG. 1B having been fully removed from the pouch 22 and substantially unfolded. The depicted wipe 24 is generally rectangular in shape, but any suitable shape may be used such as oval, elliptical, triangular, irregular shapes, and so forth (not shown). The wipe 24 may have any suitable unfolded width and length. For example, the wet wipe may have an unfolded length of from about 2.0 to about 80.0 centimeters or from about 10.0 to about 25.0 centimeters and an unfolded width of from about 2.0 to about 80.0 centimeters or from about 10.0 to about 25.0 centimeters. FIG. 2 shows one version of a container 40 holding multiple individually wrapped products 20 such as those of FIG. 1A, each having a sealed pouch 22 comprising wet wipes (not shown) for reducing malodor, further comprising a top end 32, a tear line 30, and a tear-away portion 36. The container 40 may be made of paperboard, plastic, foil, foam, or combinations thereof, and generally comprises a resilient rear panel 42 and a pocket element 44 defining a pocket 46. A bottom element 48 closed the bottom of the pocket 46. The pocket 46 can receive a plurality of the individually wrapped products 20. An optional closure element (not shown) may be attached to the rear panel 42 or the pocket element 44 that can be folded or pivoted over the exposed products 20 to close the container 40.

The wipe 24 may comprise a basesheet with total (dry) basis weight of from about 25 to about 120 grams per square meter and or from about 40 to about 90 grams per square meter. The basesheet may comprise a multilayer structure with, for example, laminated, bonded, or adjacent layers differing in fibers (e.g., coform with polyethylene versus coform with polypropylene or differing in the cellulosic fibers used), fiber treatments, adhesives, etc. Coform may be used for one or more layers or components, as described in U.S. Pat. No. 4,100,324 to Anderson et al. which issued Jul. 11, 1978; U.S. Pat. No. 4,604,313 to McFarland et al. which issued Aug. 5, 1986; and U.S. Pat. No. 5,350,624 which issued Sep. 27, 1994; which are herein incorporated by reference to the extent they are consistent herewith.

Figure 3:
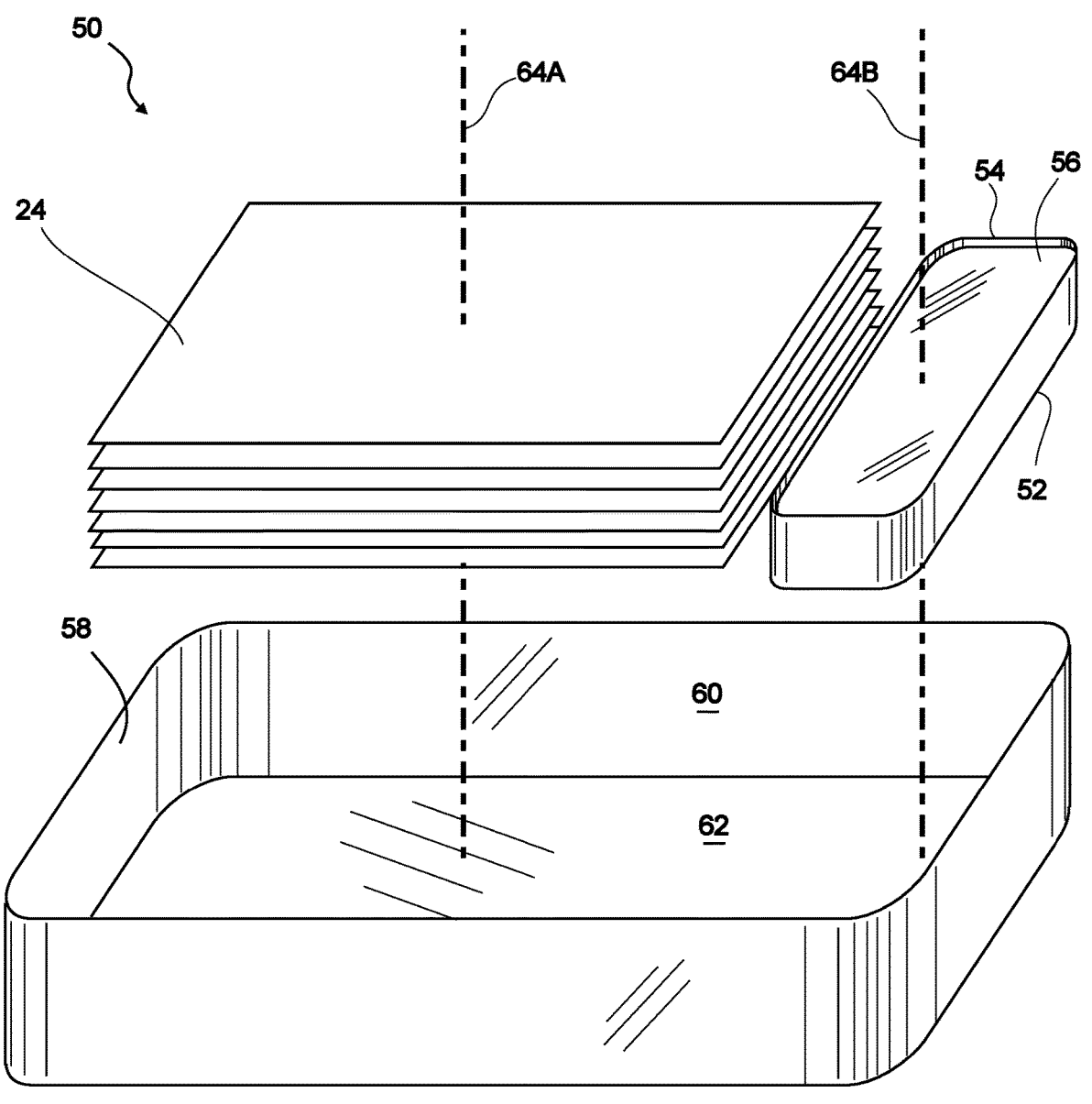
FIG. 3 shows a telescopic view of a tub for wipes and further comprising a container of a cream for application to the wipes, the cream comprising a formulation for reducing malodor.

FIG. 3 shows a telescopic view of a portion of a wipes container 50 showing a lower body 56 adapted to contain a stack of wipes 24 and a cream dispenser 52 depicted here as a simple well 54 holding a quantity of cream 56 comprising a composition effective in controlling malodor on the pudendum. The well 54 may comprise a resilient material such as a polyolefin plastic or may have flexible walls. The well 54 may be separable from the lower body 56 of the wipes container 50 or may be unitary therewith, such as a well 54 formed with the lower body 56 from plastic injection molding (not shown). The cream dispenser 52, in other embodiments, may be replaced with other known dispensers of formulations, including flexible pouches (not shown) that can release a cream by squeezing, or dispensers with mechanical means for dispensing such as pumps (not shown).

The lower body 56 has a floor 62 and side walls 60. The lower body 56 receives the stack of wipes 24 as shown along the telescoping axis 64A, and also receives the cream dispenser 52 along the parallel telescoping axis 64B.

A covering for the container 50 is not shown, but any known covering may be used such as a removable lid or a hinged lid connected to or integral with the lower body 56. In use, the covering (not shown) may be opened to allow a user to remove a wipe 24, apply a quantity of the cream 56 to the wipe 24, and then apply the wipe to the body.

Figure 4:
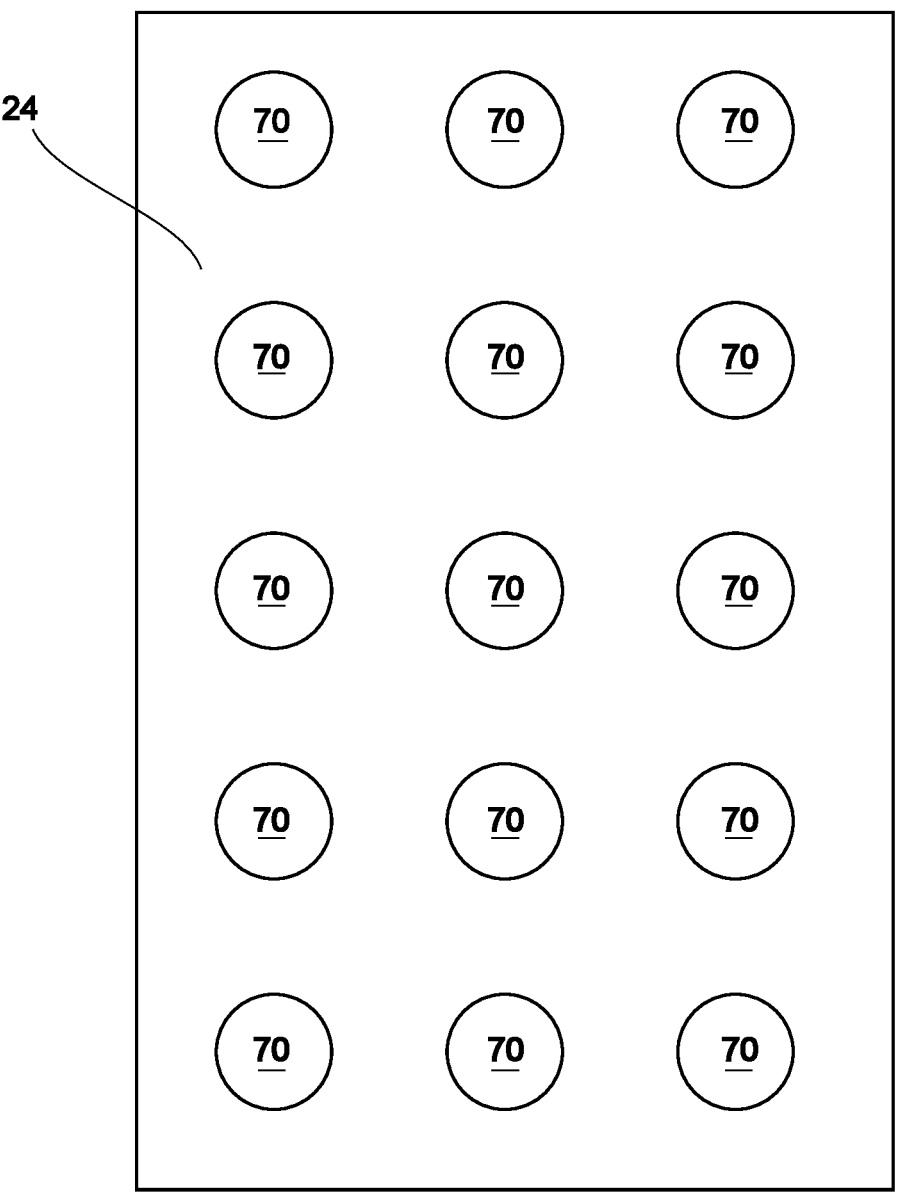
FIG. 4 shows a plan view of a wipe with discrete zones comprising an active ingredient for reducing malodor.

FIG. 4 shows a plan view of a wipe 24 with multiple discrete zones 70 comprising an active ingredient for reducing malodor. The wipe 24 itself may be a nonwoven web or other flexible porous substrate, and may be a wet wipe impregnated with an aqueous solution or may be a dry wipe. The discrete zones 70 in this embodiment are shown as circles, but they may be in any shape, size, or arrangement, such as parallel bands, irregular patches, rectangles, lines and dashes, triangular regions, and combinations thereof. The discrete zones 70 may comprise a cream, ointment, lotion, or semi-solid material comprising a composition for reducing malodor according to various embodiments described herein, The composition may comprise an acidifying agent and may, for example, comprise mandelic acid in a viscous lipophilic carrier and may have a pH from about 2.8 to about 5 or more specifically from about 3.2 to about 4.5, and more specifically still from 3.2 to 4.5. The discrete zones 70 may be substantially topical relative to the wipe 24, such that a majority of the mass in the discrete zones 70 is deposited above the upper surface of the substrate of the wipe 24 (e.g., elevated regions). Alternatively, the discrete zones 70 may be defined by matter that is substantially impregnated into the wipe 24, or may comprise both elevated regions and impregnated regions. The wipe 24 may be textured (not shown), with treated discrete zones 70 corresponding to topographical features on the wipe such as elevated structures or depressed regions (not shown).

FIGS. 5A and 5B, 6A and 6B, and 7A and 7B show experimental results regarding the suppression of TMA production by bacteria in the presence of choline as a function of time and as a function of the presence of a material according to an embodiment of the present invention. These figures are described in more detail in the discussion of Example 6 hereafter, but do show that a formulation according to an embodiment of the present invention is effective in reducing TMA production by bacterial that are frequently found on human skin.

Further Detailed Description

The acidifying components of the formulation generally include a first alpha-hydroxy acid such as mandelic acid (also known as phenylglycolic acid) and optionally a second alpha-hydroxy acid composition such as lactic acid and/or other carboxylic acids, including acids such as citric, glycolic, 2-hydroxybutyric acid, tartaric acid; gluconic acid or other isomers of pentahydroxyhexanoic acid; hydroxycaprylic acid, leucic acid (2-hydroxy-4-methylpentanoic acid), ethylglycolic acid, malic acid, and the like. U.S. Pat. No. 5,091,171, "Amphoteric Compositions and Polymeric Forms of Alpha Hydroxyacids, and Their Therapeutic Use," issued February, 1992 to Yu et al., describes alpha hydroxyl acids that can be considered for use with various embodiments of the present invention. The first alpha-hydroxy acid may have at least 7 or at least 8 carbons for each carboxylic acid group and may have a molecular weight from about 135 to about 400, more specifically from about 135 to about 250, from about 135 to about 200, or from 145 to 170. The first alpha-hydroxy acid may be monoprotic (a monocarboxylic acid) or, in some versions, diprotic (a dicarboxylic acid), though larger numbers of carboxylic acid groups may be considered. In other versions, the first alpha-hydroxy acid or both the first and second alpha-hydroxy acid may have a molecular weight of 90 or greater, 100 or greater, 120 or greater, 150 or greater, or 160 or greater. The first alpha-hydroxy acid also may have at least one aromatic ring such as a phenyl group. (Mandelic acid is the smallest alpha hydroxyl acid with an aromatic ring.) Without wishing to be bound by theory, it is believed that the first alpha-hydroxy acid as described is large enough to not rapidly penetrate into the stratum corneum of the skin, allowing it to remain present and active on the surface of the skin for a prolonged period of time, while it is also small enough to be biologically active to modify the bacterial environment on the skin and/or to maintain an acidic condition on the surface of the skin. The relatively high molecular weight and larger number of carbons per acid group in such acids may also reduce the potential for irritation to the skin.

In some embodiments, other alpha-hydroxy acids comprising aromatic rings may be used, including derivatives of mandelic acid such as those described in U.S. Pat. No. 6,777,224, "Method for Producing Optically Active Mandelic Acid Derivatives," issued Aug. 17, 2004 to Mitsuhashi et al., or the dimmers and other derivatives described in U.S. Pat. No. 5,932,619, "Method for Preventing Sexually Transmitted Diseases," issued Aug. 3, 1999 to Zaneveld et al., both of which are herein incorporated by reference to the extent that it is noncontradictory herewith.

The second alpha-hydroxy acid composition may, in some embodiments, help improve the efficacy of the first alpha-hydroxy acid while also contributing to desired acidity on the skin and optionally may also have an antimicrobial effect relative to unwanted bacteria that otherwise could contribute to an undesired fishy odor. The second alpha-hydroxy acid composition may comprise alpha-hydroxy acids having, individually or averaged, a molecular weight of about 170 or less, such as from 75 to 135, from 75 to 125, or from 80 to 85, or from 86 to 92.

The alpha-hydroxy acids in total may be present in any suitable concentration, such as 30% by weight or less, 20% by weight or less, or 10% by weight or less, and more specifically from about 0.3% to 10% (percentages in reference to chemical compositions herein will be understood to be weight percent unless otherwise indicated), from about 0.5% to about 6%, from about 1% to about 15%, or from about 0.5% to about 3.5%, or from about 0.1% to about 2.5%.

In one version, the second alpha-hydroxy acid composition comprises at least about 30%, at least about 50%, at least about 70% or at least about 93% lactic acid by weight (i.e., weight %) of lactic acid, such as from about 30% to about 90%, or from about 50% to about 95%; or from about 50% to about 95% lactic acid by weight. In one version, the second alpha-hydroxy acid is substantially all lactic acid.

Examples of formulations can include lotions, creams, gels, wipe solutions, sprays, powders, etc., with the following acidifying compositions, expressed as weight percents: 1.5% lactic acid and 0.5% mandelic acid; 2.5% lactic acid and 1% mandelic acid; 25% lactic acid and 2% mandelic acid; 10% lactic acid and 10% mandelic acid; 5% lactic acid and 4% mandelic acid; etc.

The alpha-hydroxy acids may, at least in part, be provided in time-release systems that gradually release the alpha-hydroxy acid to be effective in controlling the pH of the pudendum. Time-release technology can include microencapsulation and other systems known in the art. Time-release or other controlled release means are well known in the art. Some versions, by way of example, are described in U.S. Pat. No. 5,756,136, "Controlled Release Encapsulation Compositions," issued May 26, 1998 to Black et al.; and U.S. Pat. No. 6,835,397, "Controlled Release Encapsulated Bioactive Substances," issued Dec. 28, 2004 to Lee et al.; both of which are herein incorporated by reference to the extent that they are noncontradictory herewith.

In many embodiments, the formulations and methods disclosed herein avoid the problems of stinging or other forms of irritation that are known in some prior products. Sting-free formulations, for example, may be substantially free of ethanol, propanol, or other agents that may sting delicate tissues in the pudendal region.

While the products and methods described herein are particular suited for controlling unwanted fishy odor from the pudendum of adult or teenaged females, they may also be adapted for males in general, such as adult males. They may also be adapted for children in general, such as infants and toddlers.

Absorbent Articles

A wide variety of absorbent articles may be used to deliver formulations or assist in modifying the conditions of the pudendum to inhibit odor formation and release. Absorbent articles can include feminine pads, interlabial devices, tampons, incontinence devices such as diapers and related articles, briefs, panties, and the like. Description of exemplary products can be found in, by way of example only, the following: U.S. Pat. No. 7,201,743, "Incontinence Diaper for Adults," issued Apr. 10, 2007 to Rohrl; U.S. Pat. No. 6,454,751, "Absorbent Articles Having Hinged Fasteners," issued Sep. 24, 2002 to Olson; U.S. Pat. No. 5,830,206, "Pants-Type Diaper or Sanitary Panty," issued Nov. 3, 1998 to Larsson; U.S. Pat. No. 5,620,432, "Tape tab fasteners for disposable absorbent articles," issued Apr. 15, 1997 to Goulait et al.; U.S. Pat. No. 6,620,146, "Adult Incontinence Article with Body-Shaping Elastics," Sep. 16, 2003 to Gibbs; U.S. Pat. No. 6,375,646, "Absorbent Pants-Type Diaper," issued Apr. 23, 2002 to Widlund et al.; U.S. Pat. No. 2,092,346, "Catamenial Pad," issued to Arone on Sep. 7, 1937; U.S. Pat. No. 3,905,372, "Feminine Hygiene Protective Shield," issued to Denkinger on Sep. 16, 1975; U.S. Pat. No. 2,662,527, "Sanitary Pad," issued to Jacks on Dec. 15, 1953; U.S. Pat. No. 4,631,062, "Labial Sanitary Pad," issued to Lassen et al. on Dec. 23, 1986; all of which are herein incorporated by reference to the extent that it is noncontradictory herewith.

Disposable absorbent articles generally have a body facing intake layer comprising a porous web or film, an absorbent core, and an impervious backsheet, with other optional components as is known in the art. In some versions, the intake layer is integral with the absorbent core or is not present as a distinct separate component. In some versions, the backsheet is integral with the absorbent core or similar functionality is provided by treating the absorbent core with, for example, a hydrophilic material on the outer surface.

The absorbent core can be made of any suitable liquid-absorbent materials such as comminuted wood pulp that is generally referred to as airfelt, as well as materials such as cotton; creped cellulose wadding; meltblown polymers including composites with wood fibers such as coform; chemically modified or cross-linked cellulosic fibers; synthetic fibers such as bicomponent spunbond or crimped polyester fibers; peat moss; tissue materials including tissue wraps and tissue laminates; absorbent foams; absorbent sponges; superabsorbent polymers; absorbent gelling materials; or any equivalent material or combinations of materials, or mixtures of these. The absorbent materials may comprise folded tissues, woven materials, nonwoven webs, needle punched rayon, and thin layers of foam. Absorbent portions of the product may comprise a single material or a combination of materials, such as a wrapping layer surrounding a central wadding comprised of a different absorbent material.

The backsheet may comprise a woven or nonwoven material, polymeric films such as thermoplastic films of polyethylene or polypropylene, or composite materials such as a film-coated nonwoven material. It may be flexible and adapted to fit into or attach to undergarments such as panties. It may be provided with adhesive material and may have tabs for wrapping around the sides of undergarments. Other attachment means that may cooperate with or attach to the backsheet may be used such as hook and loop attachment or other mechanical attachment means, coadhesive materials, snaps, belts, ligaments, and the like.

A suitable topsheet may be produced from materials such as woven or nonwoven webs comprising natural fibers (e.g., wood, cotton, or other cellulosic fibers), synthetic fibers (e.g., polyester, rayon, polypropylene, or polyethylene fibers) or from a combination of natural and synthetic fibers. Other woven and nonwoven materials may include apertured formed thermoplastic films, apertured plastic films, and hydroformed thermoplastic films; porous foams; reticulated foams; reticulated thermoplastic films; and thermoplastic scrims.

The topsheet may comprise an apertured formed film such as those described in U.S. Pat. No. 3,929,135, "Absorptive Structures Having Tapered Capillaries", issued to Thompson on Dec. 30, 1975; U.S. Pat. No. 4,324,246, "Disposable Absorbent Article Having A Stain Resistant Topsheet", issued to Mullane et al. on Apr. 13, 1982; U.S. Pat. No. 4,342,314, "Resilient Plastic Web Exhibiting Fiber-Like Properties", issued to Radel et al. on Aug. 3, 1982; U.S. Pat. No. 4,463,045, "Macroscopically Expanded Three-Dimensional Plastic Web Exhibiting Non-Glossy Visible Surface and Cloth-Like Tactile Impression", issued to Ahr et al. on Jul. 31, 1984; and U.S. Pat. No. 5,006,394, "Multilayer Polymeric Film" issued to Baird on Apr. 9, 1991. The topsheet, for example, may be similar or identical to the material employed by The Procter & Gamble Company of Cincinnati, Ohio known as the "DRI-WEAVE®" topsheet.

Methods of applying the acidifying compositions to the absorbent articles include spraying, blade coating, contact coating, curtain coating, application with metered rods, flexographic printing, gravure printing, ink-jet printing, other digital printing techniques, and other known methods.

Lotioned topsheets and methods of manufacturing them are described in US 20040064117, "Absorbent Article Having a Lotioned Topsheet," published Apr. 1, 2004 by Hammons et al., herein incorporated by reference to the extent that it is noncontradictory herewith.

U.S. Pat. No. 6,118,041, "Diaper Having a Lotioned Topsheet," issued Sep. 12, 2000 to Roe et al., herein incorporated by reference to the extent that it is noncontradictory herewith, describes an absorbent article worn next to the skin of a user that can transfer a lotion on the topsheet of the article to the skin of the wearer. In one version, the Roe patent describes an absorbent article with a topsheet having a lotion coating which is semi-solid or solid at 20° C. and which is partially transferable to the wearer's skin, the lotion coating comprising from about 10 to about 95% of a substantially water free emollient having a plastic or fluid consistency at 20° C., wherein the emollient contains about 5% or less water and emollient comprising a member selected from the group consisting of petroleum-based emollients, fatty acid ester emollients, alkyl ethoxylate emollients, and mixtures thereof, further comprising from about 5 to about 90% of an agent capable of immobilizing the emollient on said outer surface of the topsheet, wherein the immobilizing agent has a melting point of at least about 35° C. and is miscible with the emollient.

The immobilizing agent may comprise a member selected from the group consisting of waxes, polyhydroxy fatty acid amides, C14-C22 fatty alcohols, C12-C22 fatty acids, C12-C22 fatty alcohol ethoxylates having an average degree of ethoxylation of about 2 to about 30, and mixtures thereof. The natural fats or oils of the oil-in-water emulsion composition may be selected from the group consisting of:

avocado oil, apricot oil, babassu oil, borage oil, camellia oil, canola oil, castor oil, coconut oil, corn oil cottonseed oil, evening primrose oil, hydrogenated cottonseed oil, hydrogenated palm kernel oil, maleated soybean oil, meadowfoam oil, palm kernel oil, phospholipids, rapeseed oil, palmitic acid, stearic acid, linoleic acid, stearyl alcohol, lauryl alcohol, myristyl alcohol, behenyl alcohol, rose hip oil, sunflower oil, soybean oil, and mixtures thereof. The amount of said fats or oils used in the composition may be from about 0.5 to about 10 weight percent, and more preferably from about 1 to about 5 percent.

U.S. Pat. No. 5,607,760 to Roe, herein incorporated by reference to the extent that it is noncontradictory herewith, describes a lotion coating on the outer surface of the non-woven top sheet of an absorbent article, such as diapers, pull-on products, adult incontinence devices, and the like. A waterless lotion composition is reported to convey a desirable therapeutic or protective coating benefit and to be effective in reducing the adherence of bowel movement to the skin. The lotion is solid or semi-solid at 20° C. with a preferred melting point of about 45° C. In one version of a process for the application of the lotion to a substrate, the lotion composition is placed in a heated tank operating at a suitable temperature such as about 63° C., then sprayed onto the substrate by a spray head operating at a warmer temperature such as about 71° C. In some versions, the system of Roe can be adapted for application of formulations to prevent fishy odor described herein.

Absorbent articles capable of transferring a coated or impregnated material to the body of the wearer may be made according to the principles described in any of the following US patents: U.S. Pat. No. 3,860,003 issued to Buell on Jan. 14, 1975; U.S. Pat. No. 5,151,092 issued to Buell et al. on Sep. 29, 1992; U.S. Pat. No. 5,221,274 issued to Buell et al. on Jun. 22, 1993; U.S. Pat. No. 4,988,344 entitled "Absorbent Articles with Multiple Layer Absorbent Layers" issued to Reising, et al on Jan. 29, 1991 and U.S. Pat. No. 4,988,345 entitled "Absorbent Articles with Rapid Acquiring Absorbent Cores" issued to Reising on Jan. 29, 1991. The topsheet may comprise carded and thermally bonded web made by means well known to those skilled in the fabrics art. In one version, a suitable topsheet comprises staple length polypropylene fibers having a denier from about 1.8 to about 4. As used herein, the term "staple length fibers" refers to those fibers having a length of at least about 15.9 mm (0.625 inches). The topsheet may, for example, have a basis weight from about 14 to about 25 grams per square meter.

Absorbent articles with pressure-rupturable capsules may also be considered, including those of U.S. Pat. No. 3,585,998 issued to Hayford et al. which describes a disposable baby diaper, an interior liner of which carries an array of pressure-rupturable capsules containing baby oil. The patent teaches that it is desirable to break the capsules prior to using the diaper by applying pressure. The principle of pressure-rupturable capsules is also used in U.S. Pat. No. 3,464,413 issued to Goldfarb et al. for making bandages capable of delivering a medicinal material to an injury.

U.S. Pat. No. 3,896,807 to Buchalter describes an article impregnated with a solid oil phase of cream formulation which forms a cream upon addition of moisture thereto. In related adaptations, the approach of Buchalter could be used to provide a cream that becomes further activated by body moisture.

U.S. Pat. No. 3,489,148 to Duncan et al. teaches a baby diaper comprising a hydrophobic and oleophobic topsheet wherein a portion of the topsheet is coated with a discontinuous film of oleaginous material.

Wipes

Wipes, whether dry, wet, or in other states, can be made from any suitable substrate that provide a flexible surface useful in applying compositions described herein. The wipe may be a porous, flexible wet wipe capable of retaining and applying a liquid solution, or may be flexible dry wipe that can apply a viscous formulation form its surface onto the pudendum. Suitable materials may include nonwoven or woven fabrics, tissue paper, composite or multilayered materials, etc, The wipe may be made from a conventional towelette or wet wipe material or other materials that have been proposed for wipes such as a nonwoven fabric including materials such as spunbond webs, meltblown webs, combinations of polymeric and natural fibers such as spunlace or coform webs, needlepunched webs, hydroentangled or spunlace materials, bonded carded webs, electrospun layers, composites or multilayer fabrics, woven textiles, apertured films, and the like. Polymeric materials used in the production of nonwoven webs, woven webs, and films may include polypropylene, polyethylene, PET, nylons, and the like. Foam pads or layers may be used, including open cell and closed cell foams, such as polyurethane foams, regenerated cellulose foams, and the like.

Examples of materials that may be used in producing wipes as described herein include those disclosed in any of the following, alone or in combination: U.S. Pat. No. 5,935,880, "Dispersible Nonwoven Fabric and Method of Making Same," issued Aug. 10, 1999 to Wang et al.; U.S. Pat. No. 6,315,864, "Cloth-Like Base Sheet and Method for Making the Same," issued Nov. 13, 2001 to Anderson et al.; U.S. Pat. No. 6,416,623, "Method of Producing an Extensible Paper Having a Three-Dimensional Pattern and a Paper Produced by the Method," issued Jul. 9, 2002 to Hollmark et al.; U.S. Pat. No. 6,737,068, "Wipe Formulation," May 19, 2004, issued to Durden; U.S. Pat. No. 7,482,021, "Two-Sided Wipe for Cleaning and Drying a Skin Surface," issued Jan. 27, 2009 to Tison et al.; US 20020155281, "Pre-Moistened Wipe Product," published Oct. 24, 2002 by Lang et al. US; US 20040161991, "Non-Woven Wet Wiping," published Aug. 19, 2004 by Walton et al.; US 20050045293, "Paper Sheet Having High Absorbent Capacity and Delayed Wet-Out," published Mar. 3, 2005 by Hermans et al.; all of which are herein incorporated by reference to the extent that they are noncontradictory herewith.

Wipes for use with the formulations described herein may also be made, used, or dispensed according to any of the following: U.S. Pat. No. 5,292,581, "Wet Wipe," issued Mar. 8, 1994 to Viazmensky et al.; and U.S. Pat. No. 6,537,631, "Roll of Wet Wipes," issued Mar. 25, 2003 to Rivera et al., all of which are herein incorporated by reference to the extent that they are noncontradictory herewith.

Wipes may be provided from or in association with dispensers that provide a quantity of a formulation as described herein useful in preventing or reducing odor from the pudendum. Such a dispenser can include a combination of wipe dispenser and spray applicator for dispensing active ingredients, as described, for example, in US 20090057331, "Wipes Dispenser," published Mar. 5, 2009 by Fryan et al., herein incorporated by reference to the extent that it is noncontradictory herewith. Wipes be dispensed from containers such as plastic or metal tubs or cylinders, from flexible pouches such as resealable pouches, form cardboard or other cellulosic containers, and from other known devices for dispensing wipes. U.S. Pat. No. 6,601,737, "Baby Wipe/Rash Cream Dispenser," issued Aug. 5, 2003 to Gartenberg, herein incorporated by reference to the extent that it is noncontradictory herewith, can also be adapted to dispense an effective quantity of a viscous composition comprising acidifying agents for the reduction of fishy odor when applied to the pudendum, such that the viscous composition can be applied to a wipe from the dispenser to assist in application of the formulation to the pudendum. The wipes may be wet or dry wipes, and may be pretreated with cleansing compositions, fragrance, and the like, which can be applied in addition to the acidifying composition as described herein.

U.S. Pat. No. 5,971,142, "Absorbent Wipe Dispensing Device," issued Oct. 26, 1999 to Jones, describes an absorbent wipe dispensing device for dispensing absorbent having a wall panel adapted for removable securement to a wall, which can be adapted for use with various embodiments described herein. A container for holding a supply of absorbent wipes is slidably received within the device which has an opening through it to allow for passage of absorbent wipes.

In one embodiment, individually enclosed wipes are provided, similar to known towelettes such as those discussed in WO/2003/051227, "Feminine Wipe for Symptomatic Treatment of Vaginitis," published Jun. 23, 2003 by Syed Rizvi, herein incorporated by reference to the extent that it is noncontradictory herewith. Such individual wipes may have dimensions such as 8×5.25 inch rectangles, or more generally, rectangles or other shapes with a first dimension and a second orthogonal dimension generally aligned with the major axes of the shape (e.g., the length of the sides of a rectangle) ranging from about 4 cm to about 40 cm, or from about 9 cm to about 30 cm. The aspect ratio (e.g., the length divided by the width, with the longer dimension being taken as the length) may be about 1, or from about 1 to about 1.6, or from about 1 to about 2.5, or about 1.1 or greater, or less than 3, by way of example. The wipe may be folded into smaller dimensions prior to use, and may be packaged or stored prior to consumer purchase with individual folded wipe dimensions with first and second orthogonal dimensions ranging from about 2 cm to about 18 cm, or from about 4 cm to about 12 cm, or less than about 13 cm, with an aspect ratio of from about 1, or from about 1 to about 1.6, or from about 1 to about 2.5, or about 1.1 or greater, or less than about 2. A pouch into which a folded wipe is placed may have similar but slightly greater dimensions than the wipe itself, with at least one dimension of the pouch being larger than the corresponding dimension of the wipe contained therein by no more than about 5%, about 10%, about 15%, or about 25% of the corresponding dimension of the wipe. The amount of fluid contained in the pouch may equal the amount of fluid that a saturated or less-than-saturated wipe can hold and may be carried completely by the wipe during manufacturing (i.e., no additional fluid is added to the pouch beyond what is carried by the wipe itself). Alternatively, the pouch may contain additional fluid that is placed in the pouch in addition to what the wipe carries prior to contact with the pouch, or the wipe may be substantially dry prior to placement in the pouch and may then be combined with fluid prior to sealing of the pouch.

In yet another version, a substantially dry wipe may be placed in a sealed pouch, after which liquid is injected or otherwise introduced into the pouch via, for example, a one-way flow valve or other means, optionally followed by additional sealing to prevent leakage. The amount of fluid contained in the pouch may range, by way of example only, from about 1 ml to 50 ml, from about 2 ml to about 25 ml, or from about 5 ml to about 10 ml. Alternatively, the amount of liquid present in the pouch or contained in any wipe may have a mass equal to about 10% or more, about 30% or more, about 60% or more, about 80% or more, from about 30% to about 300%, from about 50% to about 200%, or from about 70% to about 150%, of the mass of the dry wipe.

In one embodiment, the wipes are delivered in a flexible or rigid container integral with a formulation dispenser for applying an odor-controlling low-pH formulation on the wipes or the pudendum directly. The formulation dispenser can be a tab or other closure element on a pouch that contains a viscous composition that can be squeezed out through an opening onto a wipe or onto the fingers. In a related embodiment, the opening of a tab to access the contents of a container of wipes may also open a seal for a quantity of a viscous formulation to be applied to the wipe.

Other Product Forms

A variety of other product forms can be considered. Single-use sponges in individual wraps can be used, for example, with instructions and indicia similar to those for wipe products. The sponge may be polyurethane, regenerated cellulose, and other known sponge materials. The compositions described herein may be impregnated in the sponge or applied shortly prior to use. One example of related materials that can be adapted for use with the compositions described herein are the vaginal prep sponges marketed by McKesson. The sponges may be attached to a wand that can be held by the hand to apply the sponge to the pudendum conveniently. The wand may be a plastic, paper, or wooden handle. The wand and sponge may be wrapped in foil or plastic that is removed prior to use. The dimensions of the sponge may be about 3 cm to 8 cm by about 2 cm to 5 cm by about 1 cm to 3 cm. The sponge may have a raised area for gripping in the center.

Sponges on a wand could be used for external use as well as internal/vaginal use, particular if using a non shedding sponge material saturated with solution to cleanse the vagina after intercourse or at the tail end of menses.

Saturated cotton swabs (i.e., cotton-tipped swabs) can also be used to deliver the compositions described here. The size of the swab may be about 2×3 cm in size, for example, and may have a 2- to 8-mm diameter applicator stick such as a 3-mm applicator stick. The swab may packaged in a foil pack with the swab preloaded with the composition. Swabs may be used, for example, for convenient application to the interlabial folds, and may be particularly useful for women that have deep folds. Cotton balls, textiles, foam pads, or other porous substrates may also be used, and may be impregnated with a composition effective for controlling malodor, as described herein, or may be provided with a container of a composition for controlling malodor, such that the porous substrate can receive an quantity of the composition and then transfer it to the pudendal region.

Spray bottles may be used, for example, for application of the compositions described herein for post intercourse or bowel movement and also for postpartum treatments after childbirth. For example, an accordion pleated plastic bottle could be provided with a tablet inside with an effervescent composition that rapidly dissolves when water is added. After adding water, the product could function like a bidet in a bottle. Such a bottle could be collapsed when empty for convenience storage and reuse. The "bidet tablets" and bottles could be provided separately (e.g., the tablets could be provided in a blister pack).

In another embodiment, the compositions describes herein could be provided on a porous web such as a nonwoven web or paper web, including substrates similar to those used for dryer sheets in clothing care. The thin, weblike substrate pretreated with the active ingredients useful for controlling fishy odor may be dry initially but activated with moisture, or may be provided in an emulsion or ointment that does not require significant moisture to become effective in controlling pH on the pudendum. Such a sheet may be wrapped around, placed in, or otherwise attached to a feminine pad, underwear or other article that is placed adjacent to the pudendum.

In one version, active ingredients described herein are applied to tissue paper marketed as toilet paper, such as a toilet paper for female use. In wiping, small quantities of pH controlling agents can be left on the pudendum to assist on controlling the pH thereon and in preventing fishy odor or other malodors. In one related embodiment, "his and hers" rolls of toilet paper can be marketed in which the "hers" rolls are pretreated with a composition for delivering one or more alpha-hydroxy acids such as mandelic acid for use in controlling malodor arising from the pudendum.

Feminine pads or wipes can also be provided that can be held or placed in contact with the pudendum for a short period of time such as about 2 hours or less, about 1 hour or less, about 30 minutes or less, or about 10 minutes or less, such as about 10 minutes to 60 minutes or about 15 minutes to about 45 minutes. Such pads or wipes may be adapted to fit into the folds of the pudendum to deliver active ingredients for pH control. A pretreated wipe may be placed on another pad or other article for improved contact.

Active ingredients in powder form may be delivered in a spray such as a propellant-delivered powder spray may be directed to spray an article such as the crotch of underwear or the pudendum-contacting portion of an absorbent article, or may be used to spray directly on the body. Propellant-free application using a manually operated pump may be considered, wherein air, for example, entrains particulates in the dry powder.

Tampons may also be considered. Such tampons may be provided with powder in the core of the tampon.

Further Embodiments

Numerous known compounds may also be present in various formulations that are within the scope of the present invention. For example, botanical extracts may be present in effective or trace amounts. Such extracts may include, for example, extracts from *Yucca schidigera* extract, aloe vera, avocado, grapeseed, lavender, lemon, and the like. The products of the present invention may also comprise enzymes such as digestive enzymes. Also present may be useful bacteria in, for example, pro-biotic formulations. In some embodiments, microencapsulated beneficial microorganisms may be present, including lactic-acid producing microbes.

The products and methods of the present invention may also be adopted in combination with other known treatments, such as the treatments for vulvar dystrophy described in U.S. Pat. No. 4,150,128, "Method of Treating Atrophic Vulvar Dystrophy," issued Apr. 17, 1979 to Jasionowski, herein incorporated by reference to the extent that it is noncontradictory herewith. Jasionowski describes pharmaceutical formulations comprising a pharmaceutically acceptable hydrophilic ointment base containing a suspension of progesterone (Pregn-4-ene, 3,20-dione) or other progestins dissolved in vegetable oil is topically applied to an area afflicted with vulvar dystrophy. Plant estrogens, including those obtained from soy and black cohosh, may also be considered.

Many alternate product formats can be considered. For example, the compositions of the present invention may be provided not only in wipes or creams, but also as vaginal suppositories to provide ongoing release of active ingredients for the pudendal area. The compositions of the present invention may also be applied to absorbent articles such as sanitary napkins, feminine pads, incontinence pads, pantiliners, tampons, and the like. The compositions of the present invention may be delivered via wet wipes, wetted sponges, strips of nonwoven materials or other flexible materials attached to the underwear or temporarily held or wiped against the body, etc. The compositions may also be delivered by means of an aerosol spray, a non-aerosol spray such as a manually pumped spray bottle, a roller with a rolling head that delivers liquid ingredients from a liquid reservoir, a gel stick, and the like, including, for example, a tubular delivery device with a twist-click elevator mechanism in which turning of a lower portion of the device ratchets up an elevator that expels a cream or gel from an orifice on a delivery head for application to the body, similar to the delivery pen used for the Willow-Bark-to-Go anti-acne treatment of Boscia (Yokohama, Japan).

The feminine treatment composition may be applied in a variety of means to deliver active ingredients to the exterior surface of the user. These delivery means may include feminine pads (a term intended to comprise sanitary napkins, pantiliners, thong liners, and a variety of menstrual pads and incontinence products). The delivery means may also comprise wipes, particularly wet wipes, that are used to deliver active ingredients in a formulation to the exterior body of the user in the pudendum or adjacent regions. Moist or pretreated liners may also be placed in contact with the body for a period of time, similar to or in conjunction with the use of feminine pads (e.g., pantiliners). These may be applied during the day, including throughout the day or for brief periods of time, such as for 1 minute or longer, 5 minutes or longer, or 20 minutes or longer, including, for example from 10 minutes to 12 hours, from 1 hour to 6 hours, or for about 1 hour to 24 hours, or less than about any of the following: 24 hours, 6 hours, 2 hours, 1 hours, 10 minutes, 5 minutes, 1 minute, 30 seconds, or 15 seconds.

The feminine treatment composition may be generally applied in any known form such as in the form of a spray or a viscous formulation for application by means other than conventional spraying. Such a viscous formulation may comprise a cream (generally understood to comprise an emulsion such as an oil/water emulsion, including oil-in-water and water-in-oil emulsions) such as those that may be described as a moisturizer, lotion, liniment, ointment, salve, etc. The viscous formulation may also appear to be a jelly, including a single-phase or multi-phase viscous fluid such as a gel optionally displaying viscoelasticity. The viscous formulation may be characterized by being flowable under shear stress, but may have a yield stress such that at very low shear stress levels, the formulation substantially does not flow. In some cases, the yield stress may be sufficiently high such that a quantity of the viscous formulation at room temperature (22° C.) maybe applied to a substantially vertical section of human skin without immediately and noticeably flowing under the influence of gravity alone (specifically, the quantity may be sufficient to coat a 3 cm diameter circular section of dry, glabrous skin such as skin on the upper thigh to a depth of about 2 mm without visible migration of the viscous formulation after 3 minutes of gravitation pull while the skin is held substantially still in a vertical orientation). The viscous formulation may also comprise a substantial quantity of void space or gaseous bubbles and may be in the form of a foam, a multiphase gel, etc. The formulation may also be provided as a solid or semisolid material such as a soluble polymeric film or other film capable of releasing active ingredients in use, including films comprising slow-release polymeric substrates. Slow-release polymers for releasing active ingredients may be used in any other known form as well. The formulation may also be provided as a wash, as a douche product, as a suppository, as a coating, liquid, vaginal capsule, vaginal tablet, vaginal film, vaginal sponge, vaginal ovule, etc., provided that it is adapted to release active ingredients to the exterior skin of the user. The formulation may also be applied to a vaginal insert, tampon, wipe or pad, and then administered to the vagina, provided that active ingredients can be delivered therefrom to the exterior surfaces of the body adjacent the vagina.

For formulations comprising gels, although a variety of compounds may be employed, water is usually employed as the dispersion medium for the gel to optimize biocompatibility. Other possible dispersion mediums include non-aqueous solvents, including glycols, such as propylene glycol, butylene glycol, triethylene glycol, hexylene glycol, polyethylene glycols, ethoxydiglycol, and dipropyleneglycol; alcohols, such as ethanol, n-propanol, and isopropanol; triglycerides; ethyl acetate; acetone; triacetin; and combinations thereof. Typically, the dispersion medium (e.g., water) constitutes greater than about 75 wt/vol %, in some embodiments greater than about 90 wt/vol %, and in some embodiments, from about 95 wt/vol % to about 99 wt/vol % of the vaginal treatment composition.

The disperse phase of the gel may be formed from any of a variety of different gelling agents, including temperature responsive ("thermogelling") compounds, ion responsive compounds, and so forth. Thermogelling systems, for instance, respond to a change in temperature (e.g., increase in temperature) by changing from a liquid to a gel. Generally speaking, the temperature range of interest is from about 25.degree. C. and 40.degree. C., in some embodiments from about 35.degree. C. and 39.degree. C., and in one particular embodiment, at the human body temperature (about 37.degree. C.). Compositions that change state at about this temperature are useful because they will remain in a body cavity, for example, after they have been delivered. Any of a variety of thermogelling compounds that are capable of gelling when applied to the vagina may be used in the present invention. In some cases, thermogelling block copolymers, graft copolymers, and/or homopolymers may be employed. For example, polyoxyalkylene block copolymers may be used in some embodiments of the present invention to form a thermo-gelling composition. The term "polyoxyalkylene block copolymers" refers to copolymers of alkylene oxides, such as ethylene oxide and propylene oxide, which form a gel when dispersed in water in a sufficient concentration. Some suitable polyoxyalkylene block copolymers include polyoxybutylene block copolymers and polyoxyethylene/polyoxypropylene block copolymers ("EO/PO" block copolymers), such as described in U.S. Patent Application Publication No. 2003/0204180 to Huang, et al., which is incorporated herein in its entirety by reference thereto for all purposes. For instance, exemplary polyoxyalkylene block copolymers include polyoxyethylene/polyoxypropylene block copolymers (EO/PO block copolymers), etc.

Any suitable gelling agent, including gellan and other polymers and polysaccharides, may be used, including those described in U.S. Pat. No. 7,619,008, "Xylitol for Treatment of Vaginal Infections," issued Nov. 17, 2009 to Yang et al., herein incorporated by reference to the extent that it is noncontradictory herewith.

Preservatives and Antimicrobial Agents

Additional preservatives or antimicrobial agents may be provided in the formulations and systems described herein. Such agents may include cetylpyridinium chloride, parabens e.g., (methyl paraben, ethyl paraben), imidazolidinyl urea, propyl benzoate, sodium benzoatre, potassium sorbate, and the like. Other antimicrobial or bacteriostatic agents that may be considered include, by way of example only, bigua-nide, chitosan derivatives, silver nanoparticles or other sil-ver-based compositions and products capable of releasing silver ions, and the like. Nisin, a polycyclic peptide anti-bacterial agent, may also be incorporate in some embodi-ments of the formulations of the present invention.

Rheology Modifying Ingredients

Many known rheology modifiers can be considered to obtain desired properties, particularly the bioadhesive prop-erties of some embodiments. Gums such as guar gum or xanthan gum or other industrial gums, polyvinyl alcohols, polyacrylates, cellulose-derived polymers such as car-boxymethylcellise or hydroxyalkylcellulose polymers, Laponite, clays, carboxomer polymers, and numerous other compounds can be considered. Silicone elastomers can be considered, including those described in U.S. Ser. No. 09/613,266 (P&G).

Known bioadhesive polymers may be used as part of the carrier system, including polyolprepolymers from Barnet Products Group (Englewood Cliffs, New Jersey) and related compounds such as Barnet's Topicare® Delivery Com-pounds and related liquid polymers. Barnet's polyolprepoly-mers are polyalkalene glycol-based polyurethane polymers suitable for use as skin care agents that can hold active ingredients on the surface of the skin. They do not absorb substantially into the skin and can remain in place for a prolonged period of time, being capable of forming a liquid reservoir on the skin. Specific products include polyolpre-polymer-2 (PP-2), polyolprepolymer-14 (PP-14), and poly-olprepolymer-15 (PP-15). PP-2 is a lipophilic mixture of liquid hydroxy-terminated polymers in polypropylene gly-col having oligomers with a molecular weight range of 1,500 to 10,000 and an average molecular weight of about 4,000 and an HLB in the range of 12-14. At 35° C., it has a reported viscosity of about 2500 to 4000 cps. PP-14 is similar but has a higher molecular weight of about 18,000 and is more lipophilic. It has an HLB of about 11-13. At 35° C., it has a reported viscosity of about 2500 to 6000 cps. PP-15 is a mixture of liquid hydroxy-terminated polymers in polyeth-ylene glycol. It has a molecular weight of about 1,800 and is soluble in water and alcohol and can be used in aqueous systems with hydrophilic components. At 35° C., it has a reported viscosity of about 2500 to 5000 cps. See "Polyol-prepolymers: Properties and Use in Cosmetic Products—Technical Manual," Bertek Pharmaceuticals, a subsidiary of Mylan Laboratories (Englewood Cliffs, New Jersey), 1996.

The aforementioned polyolprepolymers are believed to be particularly useful in enhancing the efficacy of active ingre-dients such as alpha-hydroxy acids by holding them on the epidermis level and reducing irritation.

Bioadhesive materials useful for some of the embodi-ments described herein may include those discussed in U.S. Pat. No. 6,479,045, "Vaginal pH Buffering for Preventing Miscarriage and Premature Labor, by Treating or Preventing Bacterial Vaginosis," published Nov. 12, 2002 by Bologna et al. The Bologna patent discusses water-insoluble but water-swellable cross-linked polycarboxylic acid polymers that may be used in vaginal treatments. For some versions of the present materials and methods, the bioadhesives may be modified to comprise suitable alpha hydroxy acids and other agents, and then marketed as a solution for the problem of fishy odor by application to the pudendum as opposed to the vagina.

Skin Benefit Agents

Non-limiting examples of skin benefit agents that may be considered for use herein are described in The CTFA Cos-metic Ingredient Handbook, 2nd Edition (1992), which includes a wide variety of ingredients commonly used in the skin care industry, and which may be suitable for use in various embodiments of the present invention. Non-limiting examples of skin benefit agents include absorbents, aesthetic components such as fragrances, pigments, natural extrac-tives such as witch hazel or aloe vera, colorings/colorants, essential oils, skin sensates, astringents, etc. (e.g., clove oil, menthol, camphor, eucalyptus oil, eugenol, menthyl lactate, witch hazel distillate), anti-caking agents, antimicrobial agents (e.g., iodopropyl butylcarbamate), antioxidants, colo-rants, cosmetic astringents, cosmetic biocides, drug astrin-gents, external analgesics, opacifying agents, pH adjusters, skin-conditioning and/or moisturizing agents, i.e. glycerin, skin soothing and/or healing agents (e.g., panthenol and derivatives (e.g., ethyl panthenol), pantothenic acid and its derivatives, allantoin, bisabolol, and dipotassium glycyr-rhizinate), retinoids, (e.g. retinol palmitate), tocopheryl nicotinate, skin treating agents, vitamins and derivatives thereof. It is to be understood that the actives useful herein can in some instances provide more than one benefit or operate via more than one mode of action. Therefore, classifications herein are made for the sake of convenience and are not intended to limit the active to that particular application or applications listed.

Moisturizers may include urea, which may also be used in combination with lactic acid for effective moisturizing activ-ity.

Foam Embodiments

In some embodiments, the active ingredients are delivered to the body while in a foam state, such as stable foam, for example, that is produced with or without a propellant. In some versions, a foam is dispensed from a dispenser such as a propellant-free dispenser with pumping action to create the foam from a composition in a foamable carrier, and then applied to a wipe or other substrate, or applied to the hand of the user or otherwise delivered to the pudendum. Propel-lant-driving foam generators may also be used to deliver the composition in the form of a foam.

Active ingredients in a foam may be dispensed for sub-sequent placement on a dry wipe, a pre-moistened wipe, or other soft, flexible applicator (e.g., an object about 3-fingers wide or 4 to 10 cm wide) or a finger condom wipe or other object to used for application of the foam-based composition to the pudendum. The foam can be a non-propellant foam. A foam with a suitable stiffness or yield stress can be applied to the pudendum in any manner of methods for sustained adherence and contact with the body.

Examples of foam-based systems are described in U.S. Pat. No. 6,818,204, "Stable Foam for Use in Disposable Wipe," issued to Lapidus on Nov. 16, 2004, herein incorporated by reference to the extent that it is noncontradictory herewith. The Lapidus patent, whose teachings may be adapted for use with the present products and processes, discusses the use of compatible surfactants, e.g., nonionic, anionic, amphoteric, for use in human hygienic products. The surfactant should be capable of forming a foam when mixed with air in a finger actuated, mechanical pump foamer. Such surfactants are said to include, without limitation, those which do not irritate mucous membranes such as polyethylene 20 cetyl ether (Brij 58)™, a nonionic surfactant; sodium lauroyl sarcosinate (Hamposyl L-30)™, sodium lauryl sulfoacetate (Lathanol LAL)™ and sodium laureth sulfate (Sipon ESY)™—anionic surfactants; lauramidopropyl betaine (Monateric LMAB™), an amphoteric surfactant, as well as polysorbate 20, TEA-cocoyl glutamate, disodium cocoamphodiacetate and combinations thereof. Typically, the surfactant is said to present in an amount from about 2% to about 35% by weight, or from about 5% to about 15% by weight.

At least one foam stabilizing agent may also be present in certain foamable embodiments. Suitable foam stabilizing agents may include, without limitation, natural or synthetic gums such as xanthan gum, polyalkylene glycols such as polyethylene glycol, alkylene polyols such as glycerine and propylene glycol and combinations thereof. Typically, the foam stabilizers may be present in an amount from about 0.10% to about 5%, or from about 2% to about 4%.

In the Lapidus patent (U.S. Pat. No. 6,818,204), alkylene polyols are said to be typically employed in amounts from about 0.1% to about 10%, gums are employed in amounts ranging from about 0.05% to about 1%, and/or polyalkylene glycols are present in amounts ranging from about 0.05% to about 2%.

Preferably, the foam is produced using the F2 Finger Pump Foamer™ manufactured by AirSpray International Inc. of Pompano Beach, Fla. Such a spring-loaded valve system operates without the use of gas propellants or the like. Upon actuation, precise amounts of air and liquid are mixed, and a foam capable of maintaining its structure for a substantial length of time is dispensed. In addition, the dispenser can deliver a variable amount of foam, thereby reducing waste of the wipe agent contained therein.

A suitable foamer, by way of example, is the F2 Finger Pump Foamer™ made by AirSpray. Details of exemplary propellantless defoamers are described in U.S. Pat. No. 5,443,569, issued on Aug. 22, 1995, and U.S. Pat. No. 5,813,576, issued Sep. 29, 1998, herein incorporated by reference to the extent that it is noncontradictory herewith.

Other Ingredients

Many other ingredients may be used in the formulation provided they are not antagonistic to the intended function of the product. Such ingredients may include chelating agents such as EDTA, fragrances, viscosity modifiers, colors, opacifiers such as titanium oxide, sensory agents such as menthol or other known agents capable of producing a cooling or warming sensation on the skin; essential oils, fatty acids, proteins including various enzymes; probiotic agents to enhance growth of lactobaccili or other desirable bacteria, and the like.

Humectants and solubilizers may be used, such as butylene glycol.

In various embodiments, the formulation may be substantially free of any or all of the following: ethanol, methanol, propanol, alcohols, alcohols having 3 our fewer carbons, alcohols having 2 or fewer carbons, glycolic acid, acetic acid, critic acid, latex, spermicides, Octoxynol-9, TEA (triethylamine, a compound which may contribute to unwanted odor) or derivatives of TEA, TMA (trimethylamine), ammonia or complexes thereof, amines, protein, polyhydroxy fatty acids, polyhydroxy acids, alpha-hydroxy acids having 14 or greater carbons, fatty acids, polyhydroxy fatty acid esters (or polyhydroxy fatty acid derivatives such as esters, amides, and alcohols), benzoic acid, preservatives, perfumes, artificial colors, sodium bicarbonate, bicarbonates in solid or ionic form, retinol, or Retin-A. "Substantially free" in this context may mean lacking an effective quantity. For alcohols and acids this may be taken as less than 0.1%. In some cases, the concentration may be less than 0.05%. Xylitol or other 5-carbon sugars may be used to enhance the antimicrobial benefits of the composition. See, for example, U.S. Pat. No. 7,619,008, "Xylitol for Treatment of Vaginal Infections," issued Nov. 17, 2009 to Yang et al., previously incorporated by reference.

U.S. Pat. No. 6,440,437, "Wet Wipes Having Skin Health Benefits," issued Aug. 27, 2002 to Krzysik et al., herein incorporated by reference to the extent that it is noncontradictory herewith, describes a soft wet wipe or wipe-type product, such as a baby wipe, an adult wipe, hand wipe, a face wipe, a cosmetic wipe, a household wipe, an industrial wipe, a personal cleansing wipe, cotton balls, cotton tipped swabs, and the like, that can be made by combining the wipe or wipe-type product with an oil-in-water emulsion composition comprising a natural fat or oil, sterol or sterol derivative, humectant, emulsifying surfactant, and water. Krzysik discuss a wet wipe or wipe-type product with an oil-in-water emulsion composition comprising a natural fat or oil, sterol or sterol derivative, humectant, emulsifying surfactants and surfactant combinations having an HLB range of about 7 to about 18, and water. The composition is said to readily transfer from the wet wipe or wipe-type sheet onto the skin being contacted with the sheet to provide enhanced skin barrier benefits. The natural fat or oil used in the composition may include borage oil, avocado oil, or sunflower oil. The sterol or sterol derivative used in the composition may include soy sterol, avocado sterols, or cholesterol. The humectant used in the composition may include glycerin, sorbitol, or propylene glycol. The emulsifying surfactant used in the composition may include glyceryl stearate SE, emulsifying wax NF, or propylene glycol oleate SE. The composition may further comprise from about 0.1 to about 30 weight percent petrolatum or mineral oil.

One embodiment drawing upon the Krzysik et al. patent is a wet wipe or wipe-type product that enhances skin barrier functions having at least one layer and an oil-in-water emulsion composition. The oil-in-water emulsion composition may comprise from about 0.1 to about 30 weight percent of natural fats or oils, from about 0.1 to about 10 weight percent of sterol or sterol derivative, from about 0.1 to about 30 weight percent of humectant, from about 0.5 to about 20 weight percent of emulsifying surfactant having an HLB range from about 7 to about 18, and from about 45 to about 99.5 weight percent of water. The amount of the oil-in-water emulsion composition contained within each wet wipe or wipe-type product may range from about 150 to about 600 weight percent based on the weight of the product. This formulation can be modified according to the discoveries disclosed previously to be useful in preventing unwanted odor, including the use of suitable alpha hydroxy acids.

The lists of fats and oils, fatty acids, fatty alcohols, essential oils, and emulsifying surfactants in the Krzysik et al. patent (U.S. Pat. No. 6,440,437, previously incorporated by reference) are in particular incorporated herein by reference and may be used for various embodiments herein.

Suitable humectants may include, but are not limited to, the following materials: acetamide MEA, Aloe Vera Gel, arginine PCA, chitosan PCA, copper PCA, corn glycerides, dimethyl imidazolidinone, fructose, glucamine, glucose, glucose glutamate, glucuronic acid, glutamic acid, glycereth-7, glycereth-12, glycereth-20, glycereth-26, glycerin, honey, hydrogenated honey, hydrogenated starch hydrolysate, hydrolyzed corn starch, lactamide MEA, lactic acid, lactose lysine PCA, mannitol, methyl gluceth-10, methyl gluceth-20, PCA, PEG-2 lactamide, PEG-10 propylene glycol, polyamino sugar condensate, potassium PCA, propylene glycol, propylene glycol citrate, saccharide hydrolysate, saccharide isomerate, sodium aspartate, sodium lactate, sodium PCA, sorbitol, TEA-Lactate, TEA-PCA, urea, xylitol, and the like, as well as mixtures thereof.

Non-ionic silicone surfactants may also be used, according to US20070141127, "Wet Wipes with Natural Antimicrobial Agents," herein incorporated by reference to the extent that it is noncontradictory herewith. Suitable natural antimicrobial agents discussed therein may also be combined with the formulations described here.

U.S. Pat. No. 5,665,426 to Krzysik et al., herein incorporated by reference to the extent that it is noncontradictory herewith, describes a lotion formula that can be applied to a tissue which will remain available for transfer to the user's skin to reduce skin irritation and redness. The lotion composition includes from about 30 to about 90 weight percent of oil, from about 10 to about 40 weight percent wax, and from about 5 to about 40 weight percent of a fatty alcohol. The melting point of the lotion composition is from about 30° C. to about 70° C. The lotion was applied to the tissue via a heated rotogravure printing process.

Specifically, the formulation was pre-melted at about 56° C. and the press supply system (supply hose, doctor application head, and gravure roll) was pre-heated to about 50° C. The deposit solidified almost instantaneously on the surface of the treated tissue. Such a system can be adapted for versions of the present system to apply a lotion to a tissue, a wipe, a topsheet, or other suitable surface for subsequent transfer to the skin of a user.

In general, whether applied from a treatment on an absorbent article, from a wipe of any kind, by a spray, sponge, pads, by the fingers, or by any other means, the formulation may have the characteristics of a semi-solid at both 20° C. and at 37° C. (normal internal body temperature). For example, at 20° C., the portion of the formulation that is liquid may be from about 2% to about 60% by weight, or from about 5% to about 50% by weight, or from about 5% to about 30% by weight. Upon heating to 37° C., the liquid fraction may be from about 5% to about 80%, or from about 10% to about 75%, or from about 15% to about 70%, which may, for example, represent an increase in the relative amount of liquid present, wherein the ratio of the liquid weight percent at 37° C. to the liquid weight percent at 20° C. may be greater than 1, greater than 1.05, greater than 1.1, or greater than 1.2, such as from about 1.05 to about 20, from about 1.05 to about 10, from about 1.05 to about 6, or from about 1.20 to about 10.

In one version, the formulation may have substantially liquid properties at room temperature prior to being applied to a substrate. U.S. Pat. No. 7,169,400, "Waterless Lotion and Lotion-Treated Substrate," issued Jan. 30, 2007 to Luu et al., herein incorporated by reference to the extent that it is noncontradictory herewith, describes lotion compositions that are substantially liquid at room temperature (defined by Luu et al. as being from 20° C. to 25° C.) but which become semi-solid or substantially more viscous after application to a substrate such as a cellulosic or other polymeric web as a component of the composition is absorbed by the substrate. In one version, Luu et al. describe a lotion including a micro-emulsion, which comprises a polar emollient, a non-polar emollient, a non-ionic surfactant, and a co-surfactant wherein at least one of the emollients has substantial solubility in either cellulosic or synthetic fiber. For example, at least the polar emollient may be soluble in cellulosic fibers and the non-polar emollient may be soluble in synthetic fibers. Polar emollients may include a polyhydroxy emollient such as propylene glycol, glycol, glycerol, sorbitol, diethylene glycol, methylene glycol, poly propylene glycol, poly ethylene glycol, and the like.

Non-polar emollients may include an aromatic or linear ester, Guerbet ester, mineral oil, squalane, squalene, liquid paraffin and the like. The polar or non-polar emollient is either in the continuous outer phase or in the discontinuous internal phase of the micro-emulsion. Co-surfactants may include fatty alcohols. Preferred fatty alcohols include C12 to C18 fatty alcohols, behenyl alcohol, iso cetyl alcohol, and iso stearyl alcohol.

Non-ionic surfactants may include PEG-20 methyl glucose sesquistearate, PPG-20 methyl glucose ether, PPG-20 methyl glucose ether distearate, PEG-20 methyl glucose distearate, PEG-120 methyl glucose dioleate, ethoxylated methyl glucose having from about 10 to about 20 repeating ethoxy units, and the like. The lotion may comprise, for example, at least 10% polyalkoxy or polyhydroxy emollient; an aromatic ester, such as C12 to C15 alkyl benzoate ester or mineral oil; and may further comprise myristyl alcohol and, for example, PEG-20 methylglucose sesquistearate. Such lotions may be adapted for use with other formulations described herein and may, for example, further comprise mandelic acid.

The formulation may also comprise a plurality of other acidifying agents such as acetic acid, fumaric acid, ascorbic acid, and the like. Known medicaments may also be included, such as compositions in pharmaceutically effective concentrations for treating infections, skin disorders, and other known health conditions.

Packaging and Dispensing

Products made according to any of the embodiments of the present invention may be packaged and/or dispensed in any known way suitable for any particular product format. Wet wipes, for example, may be packaged in perforated rolls contained within flexible pouches or rigid dispensers of any kind. Wipes may also be cut and folded into known configurations such as C-folds, L-folds, M-folds, quarter folds, and the like, for dispensing wipes from various known containers. In some embodiments, each individual wet wipe is arranged in a folded configuration and stacked one on top of the other to provide a stack of wet wipes. The stack of folded wet wipes may be placed in the interior of a container, such as a plastic tub, to provide a package of wet wipes for eventual sale to the consumer. Alternatively, the wet wipes may include a continuous strip of material which has perforations between each wipe and which may be arranged in a stack or wound into a roll for dispensing.

Wipe dispensers and dispensers for other product forms may include mounted and stand-alone dispensers such as those of Klein Environmental Supplies, (Englewood Cliffs, NJ).

Wipes or absorbent articles used within the scope of the present invention may be packaged using any known wrapper, pouch, casing, or other packaging system, such as those described in U.S. Pat. No. 6,010,001, "Individual Packaging for Hygienic Wiping," issued Jan. 4, 2000 to Osborn; U.S. Pat. No. 3,062,371, "Internally Sterile Composite Package," issued to D. Patience on Nov. 6, 1962; U.S. Pat. No. 3,698,549, "Packages for Small Articles," issued to J. A. Glassman on Oct. 17, 1972; all of which herein incorporated by reference to the extent that they are noncontradictory herewith. Systems that can be adapted for use with certain embodiments of the present invention include U.S. Pat. No. 5,180,059, "Package of a Sanitary Tampon," issued to S. Shimatani and K. Shimatani on Jan. 19, 1993, which describes packaging sheets that help protect the user's hands during application of the product.

Wipes and other products may be provided in sterile heat sealable pouches. Sterilization, if desired, may be provided by gamma irradiation, microwave radiation, e-beam radiation, ultraviolet light, steam autoclaving, ethylene oxide treatment, or any other known method.

Pouches may substantially consist or comprise foil, foil laminates, polymeric films, and the like.

Wipes may also be dispensed from sealable jars such as glass or plastic jars or other resilient containers. Any known dry or wet wipe container may also be considered, including resilient plastic tubs with openings for dispensing of wipes in a pop-up manner, such as Cottonelle® wipes from Kimberly-Clark Corporation (Dallas, TX).

In one version, wipes may be co-packaged with single-use dispensers of a formulation in the form of a lotion, cream, or solution, wherein a cardboard or plastic container for wipes (e.g., a rectangular container holding plurality of wipes) is connected to a lid element by a hinge, in which the underside of the lid contains a plurality of single-use formulation containers such as pouches that can be opened by squeezing or tearing. The single-use formulation containers may be held by a pocket on the underside of the lid element, allowing them to be visible when the lid element is placed in an upright or open position, allowing both the wipes and the single-use containers to be visible and readily selected and taken by a user, as desired. This packaging embodiment may have a lid element that resembles several popular chewing gum packages such as those described in US20090150231, "Package Assembly for Multi-Modality Functional Ingredients in Chewing Gum Compositions," published Jun. 11, 2009 by Jani et al.

Directions for Use

Inidicia placed on or otherwise associated with packaging may inform users of the benefits of the product, call attention to the relationship between fishy odor and the non-pathological environment of the pudendum, provide information about the importance of maintaining the right pH in that region, and give instructions for use. Instructions for use may include, by way of example, information similar to the following:

"Directions for use. For best product performance, after showering, blow dry your bottom on a low warm setting until skin is dry. Apply the cream to the folds between your labia, up onto your clitoral hood, perineum and between your buttocks including the area around your anus.

"For best results, use the wipe to cleanse the areas of your bottom after urination, bowel movements, intercourse and rigorous activity. Reapply the cream if needed for added protection especially after showering."

Indicia may be placed on the packaging material holding a container of a composition such as an outer cardboard box, or may be placed on the container that directly holds the composition (e.g., a squeezable tube, a plastic or glass jar, a spray bottle, a foam dispenser, a tube of wipes, etc.). Alternatively or in addition, instructions for use may be associated with the product in a variety of ways other that directly printing on a package. The instructions may be provided on printed material that is distributed with the product but physically detached therefrom, or may be on a website or other information source that is associated with the product (e.g., accessible via a QR code, barcode, RFID tag, or URL printed on the package). Information about the product and its use may also be approved in promotional media such as in television commercials promoting the product. Such information may point to the surprising discovery that many cases of fishy odor are not due to pathological conditions in the vagina but are a result of proximity of sources of anaerobic bacteria to the pudendum coupled with pH lowering conditions, calling for care in maintaining a suitable pH in the pudendum.

EXAMPLES

Example 1

A viscous cream comprising lactic acid, mandelic acid, and an oil/water emulsion carrier was formulated using the following ingredients:

| | |
|---|---|
| Water | |
| Lactic acid | 8.0% |
| Mandelic acid | 4.0% |
| Glycerin | |
| Xanthan gum thickener | |
| Polyquaternium 10 | |
| Aloe vera extract | |
| Oat extract | |
| Allantoin | |
| Chamomile extract | |
| Sodium hydroxide | |
| Methylisothiazolinone (preservative) | |
| Capryl glycol | |

The pH of the formulation was 4.0.

This formulation was then tested with female subjects using an external test agency. Seventeen product summaries were collected from test subjects. The summaries are formatted on a 5 point scale with 5 being the most favorable to 1 being the least. The product was evaluated on the properties as follows, texture, feel after applied to the skin, irritability to the application area, reduction or blocked odor, how well the women liked the product and whether or not they would use the product again or recommend it to a friend. Most of the women fell between the ages of 20-50 with the exception on both extremes, the youngest being nineteen and the oldest aged sixty-five. One women was pregnant in her third trimester.

Each of 5 parameters are separately considered. All 17 gave the product a 5/5 rating in terms of texture and consistency.

The product was not irritating to the area of application. Thirteen of the 17 (76%) gave it a 5/5. Three of the 17 gave it a 4/5 or 18%. Combined 4-5/5 rating is 16/17 or 94%. One woman gave it a 3/5 rating and then explained that she had stinging upon initial application that went away quickly. She stated that overall the product worked and she would buy the product and use in the future. A point was made by several women that they had a warming sensation upon initial application that they felt meant it was working or one woman verbalized that it felt like K-Y warming gel. None of the women felt that this was a negative. Some said that they felt that it must be working.

The product reduced or blocked odor. Thirteen of the 17 (76%) gave the product a 5/5 rating for odor reduction. Three of the 17 gave a 4/5 or 18%. Combined rating of 4-5/5 is 16/17 or 94%. Of the women who gave a 4/5 in this category, there were no additional comments about why they felt it was less than a 5. One woman gave the product a 3/5. She said that it only made her feel more wet and she did not like the product. Others stated that they felt that the product helped with odor during menses, after intercourse or after working out.

For overall approval of the product, fourteen of the 17 (82%) gave it 5/5. One woman gave it a 4/5. Combined rating of 4-5/5 is 15/17 or 88%. One woman gave it a 2/5. (the one who did not like the product because it made her feel more wet). The same positive numbers were obtained when the subjects were asked if they would use this product again and recommend it to others.

Example 2

Another version of a viscous cream was made with the following ingredients:

| | |
|---|---|
| Water | |
| Lactic acid | 10.0% |
| Safflower oil | |
| Mandelic acid | 2.0% |
| Tricontyl PVP (water proofing agent) | |
| Glyceryl Stearate | |
| PEG- 100 Stearate | |
| Emulsifing Wax | |
| Caprylic Capric Triglyceride | |
| Cetyl alcohol | |
| Dimethicone | |
| Polyacryamide | |
| C13 C14 Isoparaffin | |
| Laureth-7 | |
| *Aloe vera* | |
| Allantoin | |
| Oat extract | |
| Chamomile extract | |
| Sodium Hydroxide | |
| Phenoxyrthanol (preservative) | |
| Chlorphenensin (preservative) | |
| Benzoic acid (preservative) | |
| Sorbic acid (preservative) | |
| Butylene Glycol | |

Example 3

A composition for treating fishy odor arising from the pudendum was prepared using the ingredients and weight percents shown in Table 1:

TABLE 1

| | | | | |
|---|---|---|---|---|
| Ingredients in a composition for treating fishy odor. | | | | |
| Sequence | INCI Names | Trade Names | % W/W | Suppliers |
| 1 | Water | D.I. Water | 49.60 | Open |
| 1 | Disodium EDTA | Versene Na2 | 0.100 | Open |
| 1 | Glycerin 99 vegetable | Glycerin 99 | 5.00 | Open |
| 1 | Lactic Acid 70% | Purac | 10.00 | Purac America |
| 1 | DL Mandelic acid | Mandelic Acid | 2.00 | Orient Star 310/7016402 |
| 1 | Allantoin | Allantoin | 0.10 | Open |
| 2 | Glyceryl Stearate & PEG 100 Stearate | Arlacel 165 | 3.50 | Open |
| 2 | Cetyl Alcohol | Cetyl Alcohol | 2.00 | Open |
| 2 | Dimethicone | Dow Corning 200/100 | 1.00 | Dow Corning |
| 2 | Caprylic/Capric Triglyceride | Liponate CG | 3.50 | Lipo chemical |
| 2 | Emulsifying Wax | Polawax | 3.00 | Croda |
| 2 | Tricontyl PVP | Ganez WP660 | 3.00 | ISP |
| 2 | *Carthamus Tinctorius* (safflower) Seed Oil | High oleic Safflower oil | 8.50 | Open |
| 3 | | Germazide PSB | 1.00 | |
| 3 | 50% Sodium Hydroxide | Sodium Hydroxide | 2.500 | Open |
| 3 | *Aloe Barbadensis* leaf extract | Aloe 10 Fold | 0.50 | Active organic |
| 3 | *Avena Sativa* (oat) kernel extract | Oat extract | 0.10 | " |
| 3 | *Chamomilla Recutita* (*Matricaria Matricaria*) flower extract | Chamomile extract | 0.10 | " |
| 4 | | Sepigel 305 | 2.50 | Seppic |
| 4 | PPG-12/SMDI Copolymer | Polyolperpolymer-2 | 2.00 | Barnet |

Procedures:

1. In a clean sanitized stainless steel tank, Sequence 1 ingredients were combined and mixed thoroughly to form a first mixture.
2. The first mixture was heated to 75° C. while mixing continued.
3. In a separate stainless steel tank, Sequence 2 ingredients were combined and heated to 75° C. to form a second mixture.
4. After slight cooling, when both mixtures were at 70° C., the second mixture was added gradually to the first mixture while mixing. Mixing continued for another 15 minutes to form a third mixture.
5. A cooling cycle was then started as the third mixture was cooled to 40° C. Then the Sequence 3 ingredients were added one at time in the listed order while mixing to form a fourth mixture.
6. The ingredients from Sequence 4 were then blended into the fourth mixture to form the final composition.

The final composition had a pH less than 4 and was then tested for efficacy in terms of preventing malodor. Relative to similar compositions without the PP-12 prepolymer (PPG-12), the composition was found to be surprisingly effective in preventing fishy odor from the pudendum, with a prolonged effect lasting over 24 hours. Without wishing to be bound by theory, it is believed that the prepolymer compound assists in holding the alpha-hydroxy acids of the composition off the skin and in an environment where they can be effective in maintaining a low pH and reducing the activity of anaerobic bacteria on the pudendum.

The product apparently not only diminishes existing odor on contact, but has a lasting effect that is believed to due at least in part to the combination of alpha-hydroxy acids in a lipophilic carriers. In a formulation without the prepolymer, the efficacy on the pudendum was estimated to have a duration of about 6 to 8 hours, such that fishy odor was substantially reduced or prevented after application, but would begin to return after about 8 hours. With a change in formulation to include the prepolymer from Barnet, the lasting odor control exceeded expectations and lasted upwards of 24 hours. Another surprise was the observation of an apparent cumulative effect with daily use over time, such that the interval required before the return of malodor could be detected increased significant over time beyond what was expected based on experience with related formulations without the prepolymer. In particular, the interval of time before the return of fishy odor after activities like intercourse, menses, and exercise and leaking urine was extended significantly and the intensity of the fishy odor when it did return appeared to be significantly less than expected as well. Without wishing to be bound by theory, it may be that the bacterial load is well controlled on the pudendum long after application of the product, and thus the amount of "work" to be done by reapplication of the product is lessened with regular use.

Example 4

In one prophetic example, a feminine care product is treated with the formulations previously described. The feminine care product is an absorbent disposable article that may comprise a breathable stretched elastomeric film, such as that described in U.S. Pat. No. 6,461,457, "Dimensionally Stable, Breathable, Stretch-Thinned, Elastic Films," issued Oct. 8, 2002 to Taylor et al., herein incorporated by reference to the extent that it is noncontradictory herewith, the breathable film serving as at least a portion of the skin-contacting side of the absorbent article (e.g., as an intake layer or cover layer on the article). The article may comprise a cellulosic absorbent core, an impervious film as a back layer, and other components known in the art, as described in any of the following: U.S. Pat. No. 5,795,349, "Absorbent Articles Having Panty Covering Components that Naturally Wrap the Sides of Panties," issued Aug. 18, 1998 to Lavash et al.; U.S. Pat. No. 4,738,676, "Pantiliner," issued Apr. 19, 1988 to Osborn; U.S. Pat. No. 7,601,415, "Absorbent Device Using an Apertured Nonwoven as an Acquisition Distribution Layer," issued Oct. 13, 2009; U.S. Pat. No. 6,213,993, "Self-Adhering Absorbent Article," issued Apr. 10, 2001 to Zacharias et al.; and so forth. The porous skin-contacting layer on the article may be treated, at least in part, with a formulation comprising a viscous, semisolid, or solid lipophilic components blended with an acidifying compound comprising a gentle aliphatic acid such as mandelic acid or derivatives thereof and a low-molecular weight carboxylic acid such as lactic acid. The formulation may be prepared by blending a heated molten lipophilic component (e.g., at a temperature of about 40° C. or higher, or between about 40° C. and 70° C.) with about 1% to about 20% by weight, or from about 3% to about 10% by weight, of an aqueous solution comprising the acidifying compounds, such that after blending with the lipophilic component, the resulting mixture has about 0.5% to about 3% by weight of acids. Emulsifying or stabilizing components maybe added in effective amounts to enhance the blending. The formulation may then be coated on or otherwise applied the porous web of the cover layer by known means such as impregnation, cast coating, gravure printing, flexographic printing, and the like, with an effective basis weight of the applied material corresponding to about 10 gsm (grams per square meter) or greater, such as about 50 gsm, about 100 gsm, about 250 gsm, or about 500 gsm or greater, such as from about 50 gsm to about 700 gsm, or from about 100 gsm to about 400 gsm. In contact with the body, the acidying components may be release onto the skin to elevate the pH there to an acceptable range that hinders the formation of fish odor compounds. Other components in the treatment on the absorbent article may also contribute toward that end, including antimicrobial agents.

Example 5

In a prophetic embodiment related to that of Example 4, the active ingredients are not necessarily directly on or in the body-contacting materials, but may be present in an underlying layer which can release the active ingredients to alter the environment on the skin of the wearer to reduce the formation in unwanted odors. Thus, a viscous formulation may be present beneath the body contacting material, where the body-contacting material may be a porous layer such as an apertured film or fibrous layer, and wherein the formulation may be present immediately below the body contacting material for release during use of the absorbent article. Release may be due to diffusion or migration, or may be triggered by physical or thermal means, in which case the active ingredients may be encapsulated in microcapsule or large encapsulating layers that rupture under physical compression or stress, or upon warming to some temperature above room temperature and below body temperature.

Example 6

In a report conducted and prepared by BioScreen Testing Services (Torrance, CA), various compositions were evaluated in terms of their effectiveness in suppressing the liberation of trimethylamine from gut bacteria (Report No. 644705, May 10, 2010). The report notes that BioScreen was asked to evaluate a Feminine Hygiene Cream/Solution product for its potency to inhibit the formation of trimethylamine (TMA).

A viable method was developed for the assay of trimethylamine (TMA). The method utilizes triethylamine and methanol together as internal standards and choline as the substrate for generating TMA from the bacterial species. The bacterial culture for these studies was *Clostridium sporogenes*, which was grown in house at BioScreen.

Common bacterial species present in the lower gastrointestinal tract include *Acidaminococcus, Bacteroides, Bifidobacterium, Clostridium, Coprococcus, Enterobacter, Enterococcus Escherichia, Eubacterium, Fusobacterium, Klebsiella, Lactobacillus, Megamonas, Megasphaera, Peptostreptococcus, Proteus, Ruminococcus,* and *Veillonella*. Of these, *Clostridium sporogenes* was chosen due to its reported propensity for generating TMA from substrates carrying trimethylamino moeities.

Tests were conducted with a headspace gas chromatograph to verify that *Clostridium sporogenes* bacterial could actively generating trimethylamine from a choline substrate.

Equipment for the testing included a Trace GC Ultra gas chromatograph and a Varian CP-Volamine column. An FID detector was used with 2.5 m L/min helium flow. Other details of operation are given in Table 2 below:

TABLE 2

Other settings for the GC testing.

| | |
|---|---|
| Detector: | FID |
| Range: | 10 |
| Carrier Gas Flow: | 2.5 mL/min |
| Carrier Gas | Helium |
| Split ratio: | 50 |
| Detector temperature: | 260° C. |
| Injector temperature: | 140° C. |
| Injector liner: | Split 5 mm with no glasswool plug |
| Injection volume: | 1.0 mL |
| Integrator: | Xcalibur 2.0 |
| Initial column temperature: | 40° C. |
| Hold time: | 5.0 min |
| Program rate: | 15° C./min |
| Final column temperature: | 260° C. |
| Agitator temperature: | 60° C. |

TABLE 2-continued

Other settings for the GC testing.

| | |
|---|---|
| Syringe temperature: | 80° C. |
| Final Hold time: | 5.0 min |
| Incubation time: | 10.0 min |

The bacterial species *C. sporogenes*, a species found in the lower GI tract. was inoculated into 100 mL of Fluid Thioglycolate medium and incubated at 35±2° C. for a minimum of 16 hours. At the end of incubation, the concentration of the bacterial suspension was confirmed by serial dilution in 9 mL PBS up to $10^{-7}$ and anaerobic incubation at 32.5±2.5° C. for a minimum of 48 hours. Counts were recorded from dilution plates with 25 to 250 colonies. The average counts were multiplied by the reciprocal of the dilution factor to furnish the CFU/mL of the bacterial species.

The formation of TMA from *Clostridium sporogenes* by interaction with choline substrate with the addition of 0.1 mL and 0.3 mL of Hygiene Product Solution was also investigated to arrive at the minimum amount of the Product needed for suppression of TMA formation.

Extensive testing was done to verify that TMA or methanol could be used as standards.

In results shown below, solvents, reagents and standards used are described in Table 3. Triethylamine (0.5 mL), along with methanol (0.5 mL), was dissolved in an aqueous 1% benzalkonium chloride solution in a 100 mL volumetric flask and this solution used as the dual internal standard mix.

TABLE 3

Solvents, Reagents and Standards

| Compounds | Description | Source |
|---|---|---|
| Choline bicarbonate | 80% in water | Spectrum |
| Trimethylamine | 35% in ethanol | Aldrich |
| Trimethylamine | 99.9% | Burdick and Jackson |
| Benzalkonium chloride | 52.48% | Spectrum |
| Methanol | 97% purity | EMD |
| Dimethylsulfoxide | 99.98% | VWR/BDH |
| DI Water | | In house |

Results for the evaluation of TMA suppression by a Hygiene Product Solution (the composition from Example 1) according to various embodiments of the present invention are shown in Table 4.

TABLE 4

Set up for Evaluation of Hygiene Product Potency at 1.0 mL concentration

| Sample ID | Culture Medium (mL) | Choline (mL) | Bacterial Culture (mL) | DI Water (mL) | BAC/TEA/ Methanol IS (mL) | No. of injections |
|---|---|---|---|---|---|---|
| Bacterial Culture without addition of Hygiene Product | | | | | | |
| Blank IS | 3.0 | 0.1 | | | 1.0 | 1 |
| Time 0 hrs | | 0.1 | 3.0 | 1.0 | 1.0 | 3 |
| Time 2 hrs | | 0.1 | 3.0 | 1.0 | 1.0 | 3 |
| Time 3 hrs | | 0.1 | 3.0 | 1.0 | 1.0 | 3 |
| Time 4 hrs | | 0.1 | 3.0 | 1.0 | 1.0 | 3 |
| Time 6 hrs | | 0.1 | 3.0 | 1.0 | 1.0 | 3 |
| Bacterial Culture with addition of Hygiene Product Solution (1.0 mL) | | | | | | |
| Time 0 hrs | | 0.1 | 3.0 | 1.0 | 1.0 | 3 |
| Time 2 hrs. | | 0.1 | 3.0 | 1.0 | 1.0 | 3 |

TABLE 4-continued

| Set up for Evaluation of Hygiene Product Potency at 1.0 mL concentration | | | | | |
|---|---|---|---|---|---|
| Time 3 hrs | 0.1 | 3.0 | 1.0 | 1.0 | 3 |
| Time 4 hrs | 0.1 | 3.0 | 1.0 | 1.0 | 3 |
| Time 6 hrs | 0.1 | 3.0 | 1.0 | 1.0 | 3 |

| System Suitability Standards (TMA, amount in mg) | | | | | |
|---|---|---|---|---|---|
| Sample ID | Culture Medium (mL) | Choline (mL) | TMA Std 9.75 mg/ mL (mL) | TMA Std 0.975 mg/ mL (mL) | BAC/TEA/ Methanol IS (mL) | No. of injections |
| Blank IS | 3.0 | 0.1 | | | 1.0 | 1 |
| Std 9.75 | 2.0 | 0.1 | 1.0 | | 1.0 | 1 |
| Std 4.875 | 2.5 | 0.1 | 0.5 | | 1.0 | 1 |
| Std. 1.95 | 2.8 | 0.1 | 0.2 | | 1.0 | 7 |
| Std 0.975 | 2.0 | 0.1 | | 1.0 | 1.0 | 1 |
| Std 0.4875 | 2.5 | 0.1 | | 0.5 | 1.0 | 1 |
| Std 0.195 | 2.8 | 0.1 | | 0.2 | 1.0 | 1 |
| Std 0.0975 | 2.9 | 0.1 | | 0.1 | 1.0 | 1 |

BAC = benzalkonium chloride; TEA = triethylamine

During the method development stage, it was found that addition of benzalkonium chloride, a known antibacterial compound, to the culture solution stops further reactivity of the bacterial culture with choline and hence, any experimental errors due to continued evolution of TMA before and between GC measurements is avoided.

It was observed that TMA liberation at measurable amounts commences around 2 hours after the addition of choline to the *Clostridium sporogenes* culture and steadily increases up to 6 hours. Further follow up of the reaction up to 24 hours indicated that little additional TMA was obtained after the 6 hour period.

The approach for evaluating the efficiency of the Hygiene Product Solution included utilizing a comparative experimental set up with the bacterial culture/choline mixture with and without the addition of the Hygiene Product Solution. Simultaneously, system suitability and linearity measurements employing working standards of TMA were also set up. The culture/choline reaction was followed from the time of addition of the choline reagent, at intervals of 2, 3, 4 and 6 hours from this commencement time.

At first, the effect of addition of the Hygiene Product Solution at a concentration 1.0 mL to 3.0 mL of the bacterial culture containing 0.1 mL of choline bicarbonate solution (80% aqueous) was investigated. The results of this study, using triethylamine (TEA) and methanol as internal standards, are presented in Tables 5 and 6, respectively.

TABLE 5

| Screening of Hygiene Product for Suppression of Trimethylamine (TMA) formation at a Concentration of 1.0 mL/Vial (TEA Int. Std.) | | | | | |
|---|---|---|---|---|---|
| Sample Identity | Peak Area of TMA from GC/FID | Peak Area Int. Std TEA from GC/FID | Response Factor (RF) | Conc. of TMA (mg/vial) | Average (% RSD) |
| Blank culture/choline samples (without Hygiene Product Solution) | | | | | |
| 0 hours | 22034 | 2291934 | 0.0096 | 0.1763 | |
| 0 hours | 6262 | 1344977 | 0.0047 | 0.1621 | |
| 0 hours | 5636 | 1289738 | 0.0044 | 0.1612 | 0.1665 (5.1) |
| 2 hours | 57243 | 1001257 | 0.0672 | 0.3409 | |
| 2 hours | 90416 | 894695 | 0.1011 | 0.4379 | |
| 2 hours | 72682 | 795520 | 0.0914 | 0.4102 | 0.3964 (12.6) |
| 3 hours | 446165 | 972667 | 0.4587 | 1.4614 | |
| 3 hours | 811460 | 1095777 | 0.7405 | 2.2680 | |
| 3 hours | 317356 | 672981 | 0.4716 | 1.4983 | 1.7426 (26.1) |
| 4 hours | 715862 | 946742 | 0.7561 | 2.3126 | |
| 4 hours | 907439 | 944506 | 0.9608 | 2.8982 | |
| 4 hours | 862656 | 707466 | 1.2194 | 3.6383 | 2.9497 (22.5) |
| 6 hours | 1358933 | 715723 | 1.8987 | 5.5824 | |
| 6 hours | 14434782 | 617313 | 2.3388 | 6.8419 | |
| 6 hours | 1539396 | 694965 | 2.2151 | 6.4878 | 6.3040 (10.3) |
| Culture medium/choline with Hygiene Product Solution (1 mL) added | | | | | |
| 0 hours | 20600 | 52415 | 0.3930 | 1.2734 | |
| 0 hours | 6208 | 179952 | 0.0345 | 0.2475 | |
| 0 hours | 9876 | 90641 | 0.1090 | 0.4605 | 0.6605 (82.0) |
| 2 hours | 0.00 | 7803 | 0.0000 | 0.1487 | |
| 2 hours | 0.00 | 54727 | 0.0000 | 0.1487 | |
| 2 hours | 0.00 | 48231 | 0.0000 | 0.1487 | 0.1487 (0.0) |
| 3 hours | 0.00 | 54556 | 0.0000 | 0.1487 | |
| 3 hours | 0.00 | 28354 | 0.0000 | 0.1487 | |
| 3 hours | 0.00 | 120728 | 0.0000 | 0.1487 | 0.1487 (0.0) |

TABLE 5-continued

Screening of Hygiene Product for Suppression of Trimethylamine (TMA)
formation at a Concentration of 1.0 mL/Vial (TEA Int. Std.)

| Sample Identity | Peak Area of TMA from GC/FID | Peak Area Int. Std TEA from GC/FID | Response Factor (RF) | Conc. of TMA (mg/vial) | Average (% RSD) |
|---|---|---|---|---|---|
| 4 hours | 0.00 | 169343 | 0.0000 | 0.1487 | |
| 4 hours | 4753 | 246984 | 0.0192 | 0.2038 | |
| 4 hours | 0.00 | 33644 | 0.0000 | 0.1487 | 0.1671 (19.0) |
| 6 hours | 0.00 | 18870 | 0.0000 | 0.1487 | |
| 6 hours | 0.00 | 36781 | 0.0000 | 0.1487 | |
| 6 hours | 0.00 | 11594 | 0.0000 | 0.1487 | 0.1487 (0.0) |

TABLE 6

Screening of Hygiene Product for Suppression of Trimethylamine (TMA) formation
at a Concentration of 1.0 mL/Vial (Methanol as Internal Standard)

| Sample Identity | Peak Area of TMA from GC/FID | Peak Area Int. Std (MeOH) from GC/FID | Response Factor (RF) | Conc. of TMA (mg/vial) | Average (% RSD) |
|---|---|---|---|---|---|
| Blank culture/choline samples (Hygiene Product Solution) | | | | | |
| 0 hours | 22034 | 1515332 | 0.0145 | 0.1904 | |
| 0 hours | 6262 | 1255936 | 0.0050 | 0.1630 | |
| 0 hours | 5636 | 1152265 | 0..0049 | 0.1627 | 0.1720 (9.2) |
| 2 hours | 57243 | 1179564 | 0.0570 | 0.3119 | |
| 2 hours | 90416 | 1246735 | 0.0725 | 0.3563 | |
| 2 hours | 72682 | 1259827 | 0.0577 | 0.3138 | 0.3273 (7.7) |
| 3 hours | 446165 | 1349463 | 0.3306 | 1.0949 | |
| 3 hours | 811460 | 1087570 | 0.7461 | 2.2840 | |
| 3 hours | 317356 | 1291792 | 0.2457 | 0.8518 | 1.4102 (54.3) |
| 4 hours | 715862 | 1118001 | 0.6403 | 1.9812 | |
| 4 hours | 907439 | 998037 | 0.9092 | 2.7507 | |
| 4 hours | 862656 | 622357 | 1.3861 | 4.1155 | 2.9491 (36.7) |
| 6 hours | 1358933 | 1036260 | 1.3114 | 3.9016 | |
| 6 hours | 1443782 | 1145409 | 1.2605 | 3.7560 | |
| 6 hours | 1539396 | 1033086 | 1.4901 | 4.4131 | 4.0236 (8.6) |
| Culture medium/choline with Hygiene Product Solution (1 mL) added | | | | | |
| 0 hours | 20600 | 854008 | 0.0241 | 0.2178 | |
| 0 hours | 6208 | 880909 | 0.0070 | 0.1689 | |
| 0 hours | 9876 | 831714 | 0.0119 | 0.1827 | 0.1896 (13.3) |
| 2 hours | 0.00 | 914941 | 0.0000 | 0.1487 | |
| 2 hours | 0.00 | 1190919 | 0.0000 | 0.1487 | |
| 2 hours | 0.00 | 902057 | 0.0000 | 0.1487 | 0.1487 (0.0) |
| 3 hours | 0.00 | 1026409 | 0.0000 | 0.1487 | |
| 3 hours | 0.00 | 866272 | 0.0000 | 0.1487 | |
| 3 hours | 0.00 | 966337 | 0.0000 | 0.1487 | 0.1487 (0.0) |
| 4 hours | 0.00 | 761454 | 0.0000 | 0.1487 | |
| 4 hours | 4753 | 1193731 | 0.0040 | 0.1601 | |
| 4 hours | 0.00 | 867308 | 0.0000 | 0.1487 | 0.1525 (4.3) |
| 6 hours | 0.00 | 968836 | 0.0000 | 0.1487 | |
| 6 hours | 0.00 | 791448 | 0.0000 | 0.1487 | |
| 6 hours | 0.00 | 958889 | 0.0000 | 0.1487 | 0.1487 (0.0) |

Figure 5A:
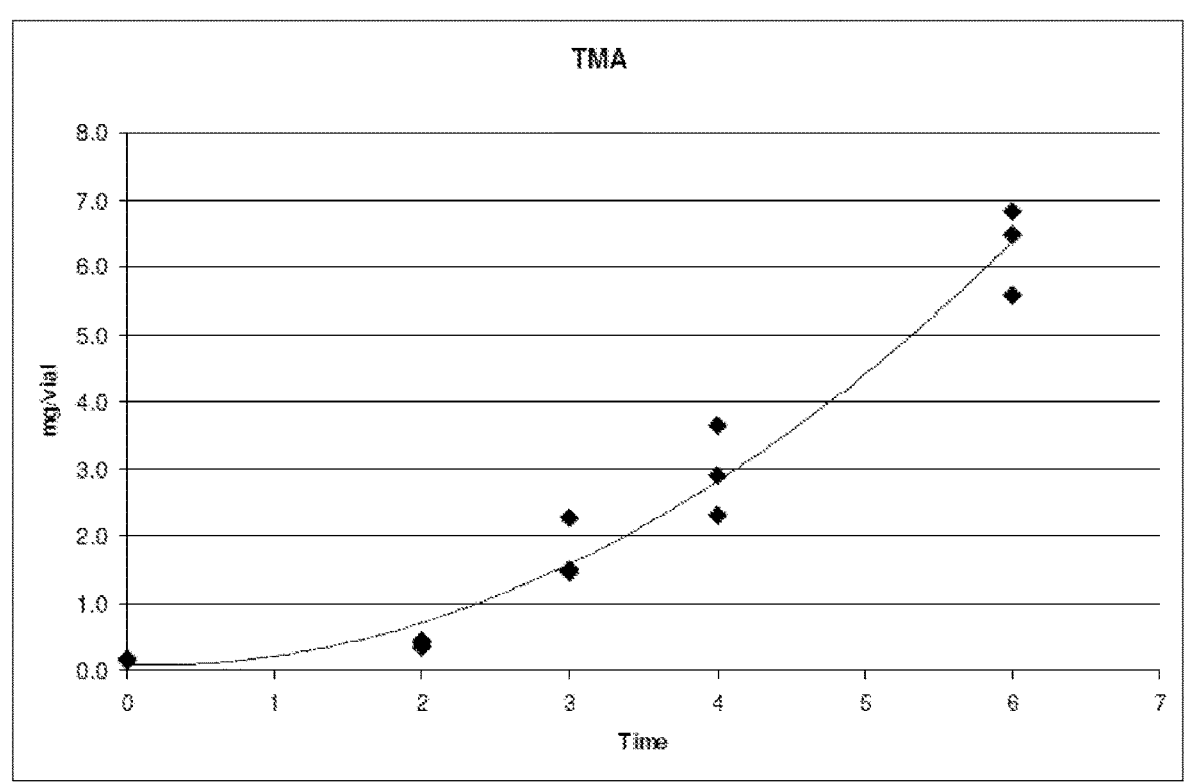
FIGS. 5A and 5B show experimental TMA versus time profiles for liquid samples containing bacteria and choline with and without a quantity of added material according to an embodiment of the present invention.
Figure 5B:
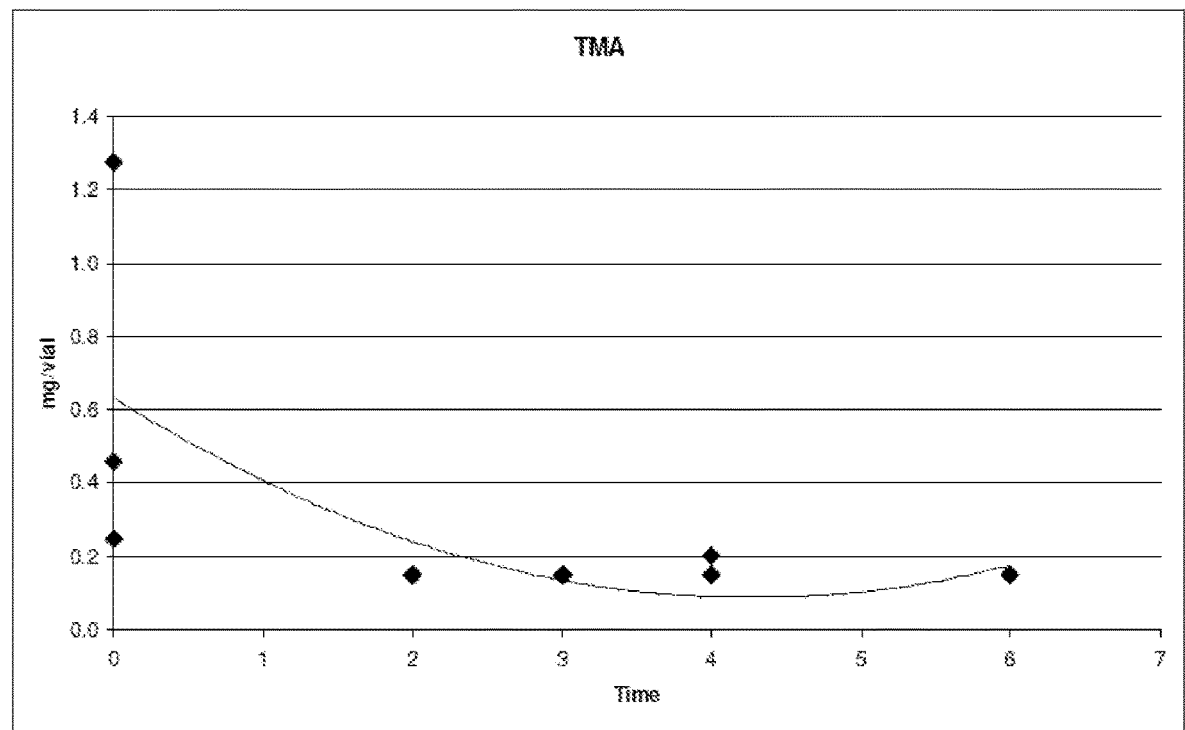
Figure 6A:
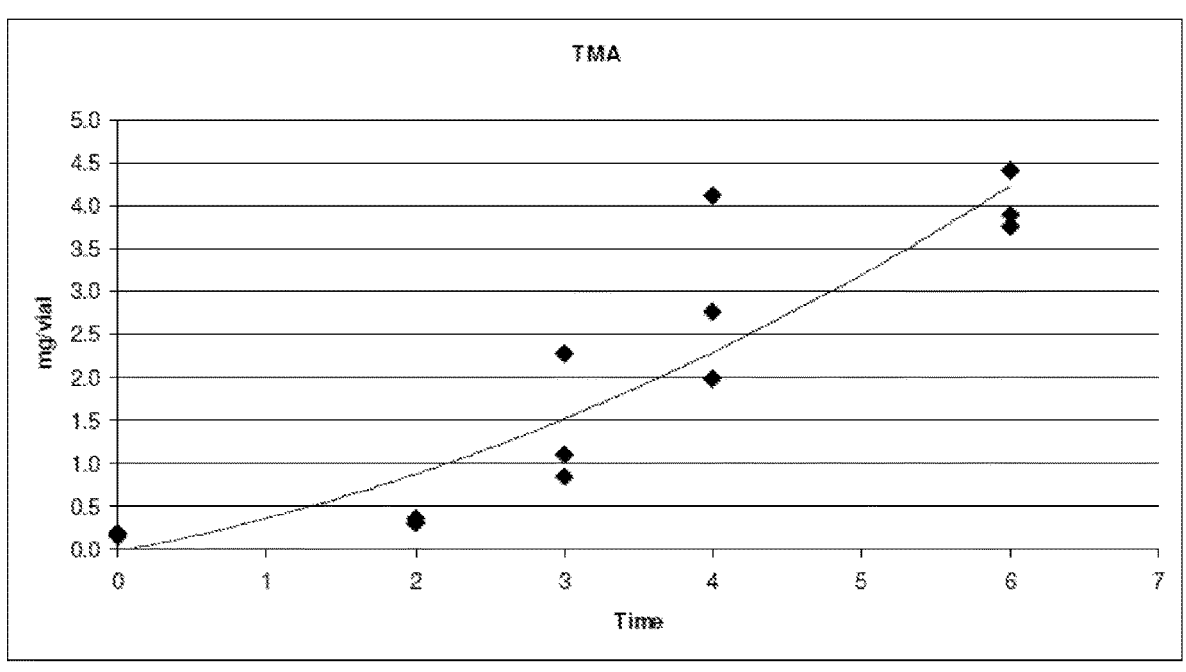
FIGS. 6A and 6B show experimental TMA versus time profiles for liquid samples containing bacteria and choline with and without a quantity of added material according to an embodiment of the present invention.
Figure 6B:
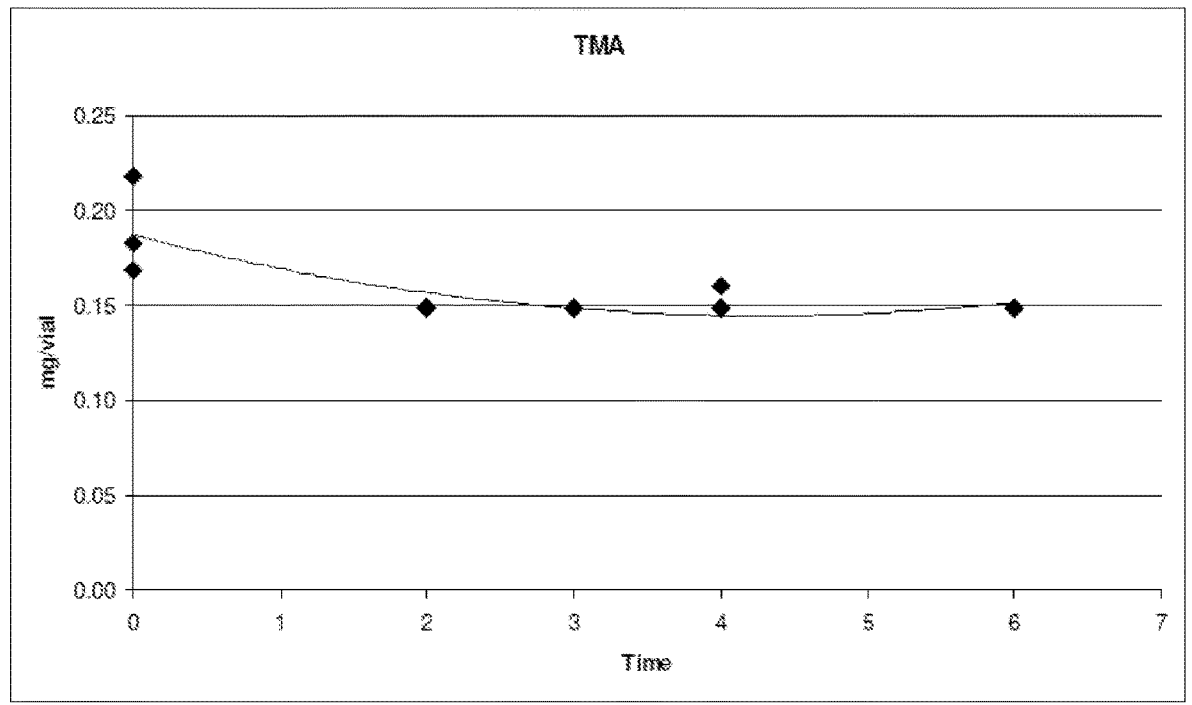

The data in Tables 5 and 6 show that formation of TMA from *Clostridium sporogenes* is completely suppressed at the Hygiene Product Solution concentration of 1.0 mL per test vial. FIGS. 5A and 5B, 6A and 6B, and 7A and 7B show graphical representations. FIGS. 5A and 5B show TMA versus time profiles for testing done without (FIG. 5A) and with (FIG. 5B) the Hygiene Product (1.0 mL concentration) of Example 1 added to vials containing bacterial culture and choline (for TEA internal standards). FIGS. 6A and 6B show TMA versus time profiles for testing done without (FIG. 6A) and with (FIG. 6B) the Hygiene Product (1.0 mL concentration) of Example 1 added to vials containing bacterial culture and choline (for methanol internal standards).

Figure 7A:
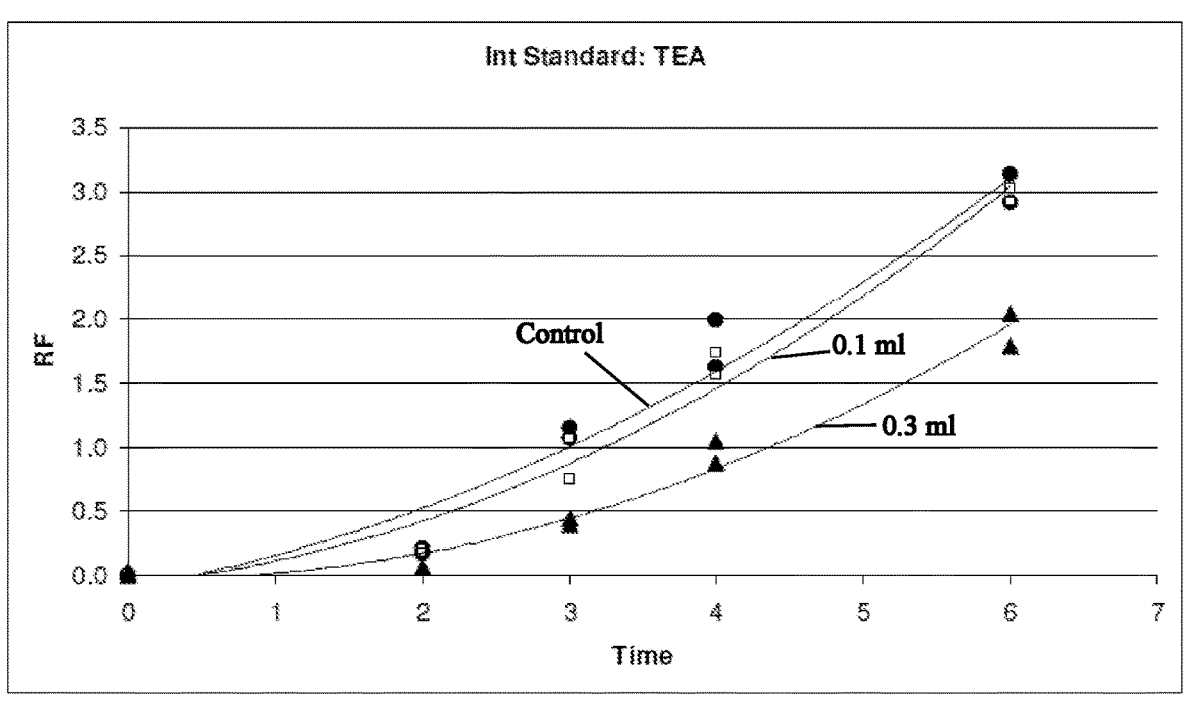
FIGS. 7A and 7B show experimental TMA versus time profiles for liquid samples containing bacteria and choline with and without a quantity of added material according to an embodiment of the present invention, further showing the effect of different concentrations of the added material.
Figure 7B:
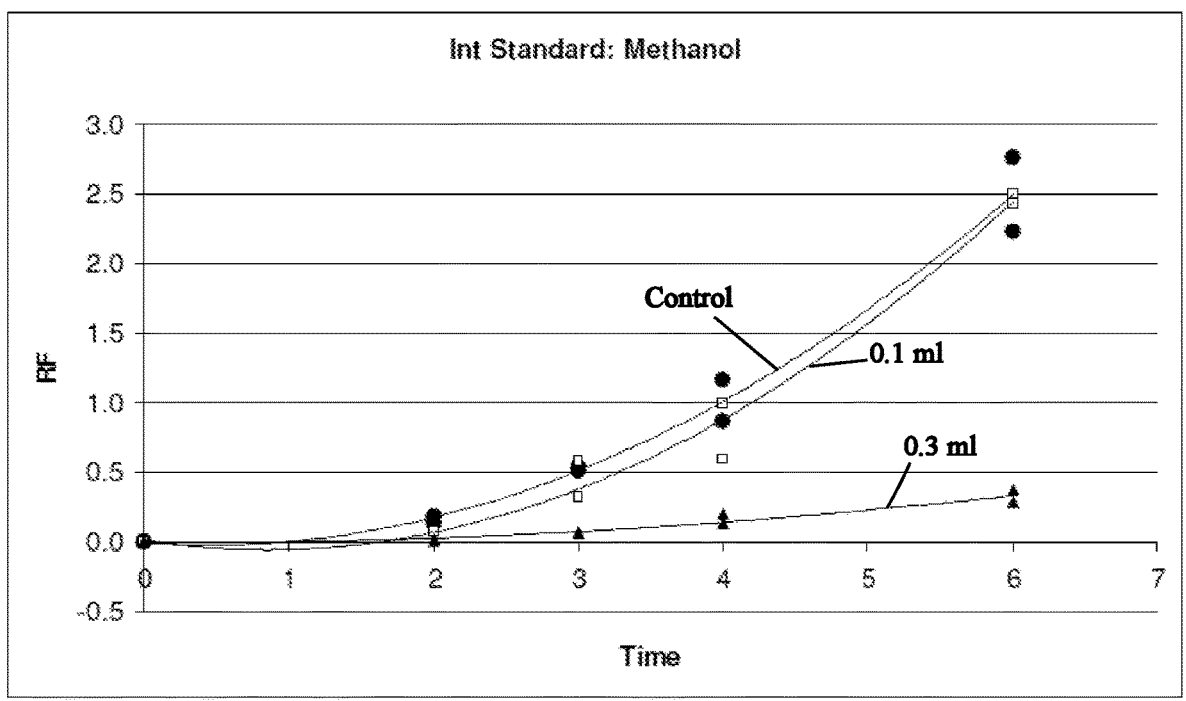

FIGS. 7A and 7B show the response factor (RF) for TMA versus time from experimental in testing of TMA concentration in vials of a bacteria-containing solution with choline with different concentrations of added material according to an embodiment of the present invention as described in Example 1. FIGS. 7A and 7B show a concentration effect for the Hygiene Product Solution in terms of its ability to suppress the formation of TMA from the bacteria. At a level of 0.1 mL Hygiene Product per vial, there was only minor suppression of TMA formation. On the other hand, at 0.3 mL level per vial, a suppression of over 60% could be observed. See Tables 7 and 8 for further details.

TABLE 7

Screening of Hygiene Product for Suppression of Trimethylamine (TMA) formation
at a Concentration of 0.1 and 0.3 mL/Vial (TEA as Internal Standard)

| Sample Identity | Peak Area of TMA from GC/FID | Peak Area Int. Std TEA from GC/FID | Response Factor (RF) | Conc. of TMA (mg/vial) | Average (% RSD) |
|---|---|---|---|---|---|
| Blank culture/choline samples (without Hygiene Product Solution) | | | | | |
| 0 hours | 0.0 | 1199841 | 0.0000 | 0.0553 | |
| 0 hours | 0.0 | | 0.0000 | 0.0553 | 0.0553 (0.) |
| 2 hours | 226372 | 1333681 | 0.1697 | 0.5466 | |
| 2 hours | 179204 | 845562 | 0.2119 | 0.6887 | 0.6076 (14.2) |
| 3 hours | 613063 | 530878 | 1.1548 | 3.3978 | |
| 3 hours | 670989 | 626892 | 1.0703 | 3.1533 | 3.2755 (5.3) |
| 4 hours | 1342568 | 825947 | 1.6255 | 4.7601 | |
| 4 hours | 1009090 | 506876 | 1.9908 | 5.8175 | 5.2888 (14.1) |
| 6 hours | 2372390 | 756959 | 3.1341 | 9.1267 | |
| 6 hours | 2191528 | 751315 | 2.9169 | 8.4981 | 8.8124 (5.0) |
| Culture medium/choline with Hygiene Product Solution (0.1 mL) added | | | | | |
| 0 hours | 8719 | 681568 | 0.0128 | 0.0923 | |
| 0 hours | 5122 | 599566 | 0.0085 | 0.0800 | 0.0862 (10.1) |
| 2 hours | 90411 | 463373 | 0.1951 | 0.6200 | |
| 2 hours | 90673 | 510613 | 0.1776 | 0.5693 | 0.5947 (6.0) |
| 3 hours | 399678 | 374049 | 1.0685 | 3.1480 | |
| 3 hours | 719013 | 949924 | 0.7569 | 2.2461 | 2.6971 (23.6) |
| 4 hours | 1044789 | 599985 | 1.7414 | 5.0955 | |
| 4 hours | 697939 | 446236 | 1.5641 | 4.5823 | 4.8389 (7.5) |
| 6 hours | 1891991 | 625092 | 3.0267 | 8.8159 | |
| 6 hours | 2340351 | 800392 | 2.9240 | 8.5186 | 8.6672 (2.4) |
| Culture medium/choline with Hygiene Product Solution (0.3 mL) added | | | | | |
| 0 hours | 0.00 | 402517 | 0.0000 | 0.0553 | |
| 0 hours | 14759 | 529344 | 0.0279 | 0.1360 | 0.0956 (59.7) |
| 2 hours | 12506 | 193472 | 0.0646 | 0.2424 | |
| 2 hours | 16007 | 254549 | 0.0629 | 0.2373 | 0.2398 (1.5) |
| 3 hours | 72904 | 182075 | 0.4004 | 1.2142 | |
| 3 hours | 79132 | 175308 | 0.4514 | 1.3618 | 1.2880 (8.1) |
| 4 hours | 142789 | 135796 | 1.0515 | 3.0987 | |
| 4 hours | 236737 | 270125 | 0.8764 | 2.5919 | 2.8453 (12.6) |
| 6 hours | 306515 | 170779 | 1.7948 | 5.2502 | |
| 6 hours | 399887 | 195678 | 2.0436 | 5.9703 | 5.6102 (9.1) |

TABLE 8

Screening of Hygiene Product for Suppression of Trimethylamine (TMA) formation
at a Concentration of 0.1 and 0.3 mL/Vial (Methanol as Internal Standard)

| Sample Identity | Peak Area of TMA from GC/FID | Peak Area Int. Std Methanol from GC/FID | Response Factor (RF) | Conc. of TMA (mg/vial) | Average (% RSD) |
|---|---|---|---|---|---|
| Blank culture/choline samples (without Griffiths Hygiene Product Solution) | | | | | |
| 0 hours | 0.00 | 1289617 | 0.0000 | 0.0553 | |
| 0 hours | 0.00 | 1280270 | 0.0000 | 0.0553 | 0.0553 (0.0) |
| 2 hours | 226372 | 1246744 | 0.1816 | 0.5808 | |
| 2 hours | 179204 | 1288664 | 0.1391 | 0.4578 | 0.5193 (16.8) |
| 3 hours | 613063 | 1201500 | 0.5102 | 1.5322 | |
| 3 hours | 670989 | 1236759 | 0.5425 | 1.6256 | 1.5789 (4.2) |
| 4 hours | 1342568 | 1153926 | 1.1635 | 3.4229 | |
| 4 hours | 1009090 | 1169900 | 0.8625 | 2.5518 | 2.9874 (20.6) |
| 6 hours | 2372390 | 1064687 | 2.2283 | 6.5048 | |
| 6 hours | 2191528 | 794532 | 2.7583 | 6.0388 | 7.2718 (14.9) |
| Culture medium/choline with Griffiths Hygiene Product Solution (0.1 mL) added (#644705) | | | | | |
| 0 hours | 6719 | 1240176 | 0.0070 | 0.0756 | |
| 0 hours | 5122 | 1259125 | 0.0041 | 0.0671 | 0.0713 (8i.5) |
| 2 hours | 90411 | 1193595 | 0.0757 | 0.2745 | |
| 2 hours | 90674 | 1223364 | 0.0741 | 0.2698 | 0.2722 (1.2) |
| 3 hours | 399678 | 1217900 | 0.3282 | 1.0051 | |
| 3 hours | 719013 | 1237478 | 0.5810 | 1.7370 | 1.3711 (37.7) |
| 4 hours | 1044789 | 1054053 | 0.9912 | 2.9243 | |

TABLE 8-continued

Screening of Hygiene Product for Suppression of Trimethylamine (TMA) formation
at a Concentration of 0.1 and 0.3 mL/Vial (Methanol as Internal Standard)

| Sample Identity | Peak Area of TMA from GC/FID | Peak Area Int. Std Methanol from GC/FID | Response Factor (RF) | Conc. of TMA (mg/vial) | Average (% RSD) |
|---|---|---|---|---|---|
| 4 hours | 697939 | 1174383 | 0.5943 | 1.7754 | 2.3499 (34.6) |
| 6 hours | 1891991 | 757336 | 2.4976 | 7.2843 | |
| 6 hours | 2340351 | 961501 | 2.4341 | 7.1005 | 7.1924 (1.8) |
| Culture medium/choline with Griffiths Hygiene Product Solution (0.3 mL) added (#644705) | | | | | |
| 0 hours | 0.00 | 931217 | 0.0000 | 0.0553 | |
| 0 hours | 5122 | 1155357 | 0.0128 | 0.0923 | 0.0738 (35.4) |
| 2 hours | 90411 | 1084704 | 0.0115 | 0.0887 | |
| 2 hours | 90674 | 1087286 | 0.0147 | 0.0979 | 0.0933 (7.0) |
| 3 hours | 399678 | 1061919 | 0.0687 | 0.2540 | |
| 3 hours | 719013 | 1088146 | 0.0727 | 0.2658 | 0.2599 (3.2) |
| 4 hours | 1044789 | 1082015 | 0.1320 | 0.4372 | |
| 4 hours | 697939 | 1174717 | 0.2015 | 0.6386 | 0.5379 (26.5) |
| 6 hours | 1891991 | 1053974 | 0.2861 | 0.8891 | |
| 6 hours | 2340351 | 1076652 | 0.3714 | 1.1303 | 1.0097 (16.9) |

The report from BioScreen offered these conclusions:

Griffiths Feminine Hygiene Product Solution (Accession #644705) is effective in suppressing the formation of trimethylamine (TMA), the main foul odor causing nitrogenous material, completely at a concentration of 1.0 mL per 3.0 mL of *Clostridium sporogenes* culture which is at a concentration of $9.6 \times 10^8$ CFU/mL.

The Hygiene Product Solution is ineffective at a concentration of 0.1 mL for 3.0 mL of the same bacterial culture.

At a concentration of 0.3 mL per 3.0 mL of the bacterial culture, around 60% suppression of TMA was observed.

It should be noted, however, that even when extremely dilute at the concentration of 0.1 mL of added material to a much larger amount of bacteria-rich liquid in a vial, the added material did not some strictly ineffective but may have had a dramatically weakened effect compared to the much stronger effect of higher doses of the material according to an embodiment of the present invention.

REMARKS

When introducing elements of aspects of the invention or the embodiments thereof, the articles "a," "an," "the," and "said" are intended to mean that there are one or more of the elements. The terms "comprising," "including," and "having" are intended to be inclusive and mean that there may be additional elements other than the listed elements.

Having described aspects of the invention in detail, it will be apparent that modifications and variations are possible without departing from the scope of aspects of the invention as defined in the appended claims. As various changes could be made in the above compositions, products, and methods without departing from the scope of aspects of the invention, it is intended that all matter contained in the above description shall be interpreted as illustrative and not in a limiting sense.

While the foregoing description makes reference to particular illustrative embodiments, these examples should not be construed as limitations. The inventive system, methods, and products can be adapted for other uses or provided in other forms not explicitly listed above, and can be modified in numerous ways within the spirit of the present disclosure. Thus, the present invention is not limited to the disclosed embodiments, but is to be accorded the widest scope consistent with the claims below.

I claim:

1. An acidic deodorant cream for application to the external human skin, comprising: water, from 2% to 5% by weight of mandelic acid, about 0.5% to about 10% of at least one fatty alcohol selected from the group consisting of stearyl alcohol, cetyl alcohol and, behenyl alcohol, and a skin soothing agent selected from the group consisting of panthenol, ethyl panthenol, pantothenic acid, allantoin, bisabolol, and dipotassium glycyrrhizinateone, wherein the acidic deodorant cream has a pH from 2.8 to 4.5, is free of EDTA and comprises less than 0.1% of methanol, ethanol, propanol, glycolic acid and bicarbonates.

2. The deodorant cream of claim 1 comprising allantoin.

3. An acidic deodorant cream for application to the external human skin, comprising: water, from 2% to 5% by weight of mandelic acid, about 0.5% to about 10% of cetyl alcohol and allantoin, wherein the acidic deodorant cream has a pH from 2.8 to 4.5, is free of EDTA and comprises less than 0.1% of methanol, ethanol, propanol, glycolic acid and bicarbonates.

* * * * *